(12) United States Patent
Fowler et al.

(10) Patent No.: US 12,025,483 B2
(45) Date of Patent: *Jul. 2, 2024

(54) TEST METHOD DEVELOPMENT FOR MASS FLOW IDENTIFICATION OF OCCLUDING SMALL PARTICULATES IN MICROLUMENS

(71) Applicant: INNOVATIVE HEALTH, Scottsdale, AZ (US)

(72) Inventors: Aaron J. Fowler, Mesa, AZ (US); Blessan C. Joseph, Chandler, AR (US); Rafal Chudzik, Peoria, AZ (US)

(73) Assignee: INNOVATIVE HEALTH, Scottsdale, AZ (US)

( * ) Notice: Subject to any disclaimer, the term of this patent is extended or adjusted under 35 U.S.C. 154(b) by 397 days.

This patent is subject to a terminal disclaimer.

(21) Appl. No.: 17/530,285

(22) PCT Filed: May 26, 2020

(86) PCT No.: PCT/US2020/034592
§ 371 (c)(1),
(2) Date: Nov. 18, 2021

(87) PCT Pub. No.: WO2020/243114
PCT Pub. Date: Dec. 3, 2020

(65) Prior Publication Data
US 2022/0241498 A1    Aug. 4, 2022

Related U.S. Application Data

(60) Provisional application No. 62/852,498, filed on May 24, 2019.

(51) Int. Cl.
| | |
|---|---|
| *G01F 25/10* | (2022.01) |
| *A61B 5/00* | (2006.01) |
| *A61B 17/34* | (2006.01) |
| *A61M 5/168* | (2006.01) |
| *G01F 1/76* | (2006.01) |
| *G01N 11/10* | (2006.01) |

(Continued)

(52) U.S. Cl.
CPC ............ *G01F 25/10* (2022.01); *A61B 5/6852* (2013.01); *A61B 17/34* (2013.01);
(Continued)

(58) Field of Classification Search
CPC .. G01F 1/76; G01F 25/10; G01F 1/74; A61M 5/16831; A61M 2005/16863;
(Continued)

(56) References Cited

U.S. PATENT DOCUMENTS

| | | |
|---|---|---|
| 3,505,843 A | 4/1970 | Kelsay |
| 4,648,270 A | 3/1987 | Johnson et al. |

(Continued)

FOREIGN PATENT DOCUMENTS

| | | | | |
|---|---|---|---|---|
| GB | 2367594 A | * | 4/2002 | .......... A61M 1/1086 |
| WO | 2006/076119 A2 | | 7/2006 | |

OTHER PUBLICATIONS

International Search Report of PCT/US20/34592 dated Jul. 27, 2020.

(Continued)

*Primary Examiner* — Benjamin R Schmitt
(74) *Attorney, Agent, or Firm* — POLSINELLI PC

(57) ABSTRACT

Method and systems for determining acceptance criteria for identification of occluding particles in a lumen of a device are provided. The methods and systems can be used in methods of identifying an occluded device in an inspection method. The acceptance criteria can be calculated based on mass flow measurements of an occluded representative device.

19 Claims, 29 Drawing Sheets

(51) Int. Cl.
*A61B 17/00* (2006.01)
*G01F 1/74* (2006.01)

(52) U.S. Cl.
CPC ........... *A61M 5/16831* (2013.01); *G01F 1/76* (2013.01); *G01N 11/10* (2013.01); *A61B 2017/00725* (2013.01); *A61B 2560/06* (2013.01); *A61M 2005/16863* (2013.01); *A61M 2205/70* (2013.01); *G01F 1/74* (2013.01)

(58) Field of Classification Search
CPC ..... A61M 2205/70; A61B 2017/00725; A61B 2560/06
See application file for complete search history.

(56) References Cited

U.S. PATENT DOCUMENTS

| | | | |
|---|---|---|---|
| 5,503,036 A | 4/1996 | Nguyen et al. | |
| 2006/0010964 A1 | 1/2006 | Sparks et al. | |
| 2009/0078047 A1 | 3/2009 | Dam | |
| 2012/0060626 A1 | 3/2012 | Zhu et al. | |
| 2013/0238138 A1 | 9/2013 | Cole et al. | |
| 2014/0378352 A1 | 12/2014 | Daridon | |
| 2015/0057538 A1* | 2/2015 | Cragg | A61M 5/007 600/431 |
| 2017/0045415 A1 | 2/2017 | Williamson | |
| 2017/0173262 A1 | 6/2017 | Veltz | |
| 2019/0275581 A1 | 9/2019 | Fernandez Orive et al. | |

OTHER PUBLICATIONS

International Search Report of PCT/US20/34592 dated Jun. 30, 2020.

Extended European Search of Regional Phase EP 20815119.1 dated May 25, 2023.

* cited by examiner

TEST METHOD DEVELOPMENT FOR MASS FLOW IDENTIFICATION OF OCCLUDING SMALL PARTICULATES IN MICROLUMENS

CROSS-REFERENCE TO RELATED APPLICATIONS

This application is a National Stage application of International Application No. PCT/US20/34592, filed May 26, 2020, and published as WO 2020/243114 on Dec. 3, 2020, which claims the benefit of U.S. Provisional Patent Application No. 62/852,498 filed May 24, 2019, the entire disclosure of which is incorporated herein by reference.

FIELD OF THE INVENTION

The present disclosure provides methods and systems for determining acceptance criteria for identification of occluding particles in a lumen of a device.

BACKGROUND OF THE INVENTION

The risk of patient injury induced by excessive loads of injected particles during hospital stays has long been understood, and reducing their occurrence is a primary goal of manufacturers and practitioners alike. A contributing factor to these complications results from potentially embolic particulates either on, in, or created by, a device, fluid, or other object introduced into the patient. The consequences of particles delivered into the bloodstream have long been understood. With an elementary understanding of anatomy, concern arises that devices placed within cardiac chambers could release potentially embolic particulates. Those discharged into the right side of the heart could occlude pulmonary arterioles (average diameter <300 micron) if large enough, potentially resulting in a pulmonary embolism (PE). Left-sided studies could direct emboli to the brain, potentially resulting in a CVA. Occlusion of penetrating arterioles (average diameter <100 micron) is of greatest concern, inducing more traumatic neuropathy. While the occurrence of these events is highly unlikely (<0.2% of procedures), and not conclusively attributable to the devices used during a study, preventing them further has led to increased scrutiny of the manufacture of anything intended to be positioned in a patient.

Therefore, there is a need for testing methods and systems capable of identifying occluding particles within lumens of medical devices.

SUMMARY OF THE INVENTION

One aspect of the present disclosure encompasses a method of determining acceptance criteria for identification of an occluding particle in a lumen of an inspected device. The method comprises isolating a defined number of one or more occluding test particles and occluding the lumen of a representative device with the defined number of particles by adhering the particles in the lumen of the representative device. The method further comprises obtaining a mass flow measurement for the occluded representative device and calculating an upper test limit mass flow rate for the occluded representative device. The upper test limit mass flow rate is the acceptance criteria, and an inspected device is occluded if a mass flow measurement for the inspected device is equal to or lower than the acceptance criteria, and the inspected device is unoccluded if the mass flow measurement in the inspected device is higher than the acceptance criteria.

The lumen of more than one representative device can be occluded. When the lumen of more than one device is occluded, the upper test limit mass flow rate is an upper boundary of a probability plot at 95/85 confidence interval or higher.

Isolating a defined number of particles can comprise suspending particles in a bead solution comprising a surfactant and aqueous polymeric adhesive and isolating one or more single particles under magnification into a bead solution. The bead solution can be a buffered bead solution comprising less than about 0.2% aqueous polymeric adhesive and less than 0.5% surfactant. Adhering the particles in the lumen of the representative device can comprise injecting the particle into the lumen of the representative device followed by drying the lumen. The lumen can be dried by incubating the device in a recirculating air oven for about 48 hours at about 65° C.

Obtaining a mass flow measurement for the representative device can comprise charging the lumen with air to a predetermined pressure, and measuring the flow of air sufficient to maintain the pressure over a preset period of time to obtain the mass flow measurement. The mass flow measurement can be obtained using a mass flow measurement instrument. The mass flow measurement instrument can be Sentinel Blackbelt Test System from Cincinnati Test Systems (CTS).

The representative device can be occluded with one occluding particle. Further, the representative device can be occluded with a 50 microns NIST traceable particle size standard polystyrene beads.

In some aspects, the device is the Biosense Webster PentaRay EP catheter and the acceptance criteria is 109.23 sccm. In other aspects, the device is Abbott (St. Jude Medical) Advisor HD Grid mapping catheters and the acceptance criteria is 157.32 sccm. In yet other aspects, the device is St. Jude Medical BRK Transseptal Needle having a length of 71 cm, and the acceptance criteria is 175.8 sccm. In yet other aspects, the device is St. Jude Medical BRK Transseptal Needle having a length of 89 cm, and the acceptance criteria is 161.1 sccm. In additional aspects, the device is St. Jude Medical BRK Transseptal Needle having a length of 98 cm, and the acceptance criteria is 154.3 sccm.

Another aspect of the present disclosure encompasses an inspection method for identification of occluding particles in a lumen of an inspected device. The method comprises determining acceptance criteria for identification of occluding particles in the lumen of the inspected device. Acceptance criteria can be determined as described above.

Once the acceptance criteria for the device is determined, a mass flow measurement is obtained for the inspected device. The mass flow measurement of the inspected device is obtained and compared to the acceptance criteria. The mass flow measurement of the inspected device can be obtained as described above and, if the mass flow measurement of the inspected device is equal to or lower than the test acceptance criteria determined, the inspected device is rejected as comprising an occlusion. The inspected device is accepted if the measured mass flow of the inspected devise is higher than the test acceptance criteria for the device.

In another aspect, the present disclosure provides a system for determining acceptance criteria for identification of occluding particles in a lumen of a device. The system comprises a mass flow measurement instrument for obtaining a mass flow measurement of a representative device. The system further comprises a computer system having at least one processor and associated memory comprising instructions for calculating an upper test limit mass flow rate for an occluded representative device and instructions which, when executed by at least one processor, cause the at least one processor to receive mass flow measurement of the occluded devices and calculate an upper test limit mass flow rate for the occluded devices. The computer system also outputs the upper test limit mass flow, wherein the upper test limit mass flow rate is the acceptance criteria, and wherein an inspected device is occluded if a mass flow measurement in the inspected device is equal to or lower than the acceptance criteria, and the inspected device is unoccluded if the mass flow measurement in the inspected device is higher than the acceptance criteria.

DETAILED DESCRIPTION

Figure 1:
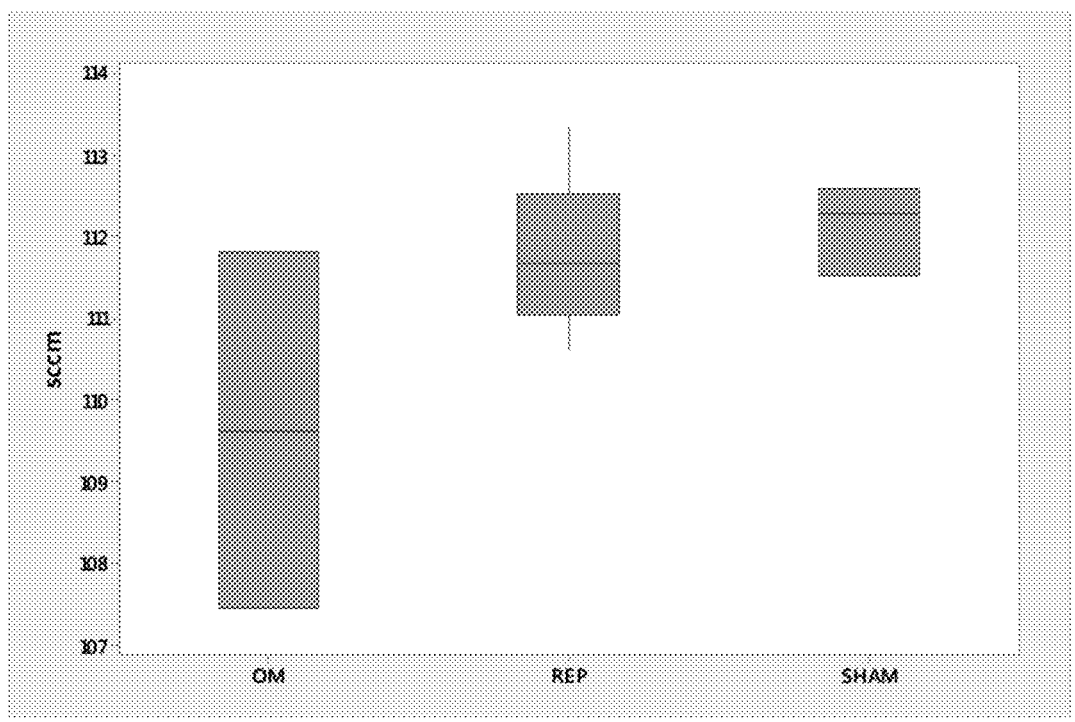
FIG. 1 depicts a plot showing mass flow readings of a device from the original manufacturer, and reprocessed untreated and sham devices treated with bead solution only.

The present disclosure encompasses a method of developing a method for inspecting a device comprising a lumen to determine if the lumen of the inspected device is occluded by one or more occluding particles. The method can be used in an in-process method of inspecting a device to accept or pass the inspected device as unoccluded, or reject the inspected device as occluded. The method is capable of detecting and rejecting an inspected device with lumens containing unacceptable levels of occluding particles. The method can be used with any device having a lumen in any field, including the medical field. A method developed according to the present disclosure is capable of identifying a single small occluding particle even within the microlumen of a medical device. Importantly, occluding particles smaller than those deemed clinically relevant can be detected using the instant methods. The ability of a test method to detect occluding particles to that resolution provides a considerable safety factor when defining acceptance criteria.

I. Method of Determining Acceptance Criteria

In one aspect, the present disclosure provides a method of determining acceptance criteria for mass flow identification of occluding particles in a lumen of a device. The acceptance criteria can then be used to accept an inspected device as unoccluded, or reject an inspected device as occluded, for example during reprocessing of medical devices for re-use. A method of the disclosure can be used to detect as few as a single occluding particle smaller than a particle deemed clinically relevant in an inspected device with a high level of confidence.

(a) Device

A method of the disclosure can be used to determine acceptance criteria for any device having a lumen. Non-limiting examples of devices include medical devices such as catheters and andoscopes, micropumps, microvalves, and microsensors, devices in the biological field such as devices for analyzing biological materials such as proteins, DNA, cells, embryos, and chemical reagents, devices for cell culture, cell separation, nucleic acid sequencing, devices in the electronics industry, for example in cooling channels in silicon chips.

In some aspects, the device is a medical device having a lumen. Medical devices that include lumens, such as catheters and endoscopes, are extensively used to perform an array of minimally invasive procedures. Catheters can be inserted into a body cavity, duct, or vessel. Functionally, they allow drainage, administration of fluids or gases, access by surgical instruments, and also perform a wide variety of other tasks depending on the type of catheter. An endoscope is an illuminated optical, typically slender and tubular instrument used to look deep into the body. Endoscopes use tubes which can be a few millimeters thick or smaller to transfer illumination in one direction and high-resolution images in real time in the other direction, and can include tubing with microlumens to also perform some procedure, resulting in minimally invasive surgeries. Placement of a catheter into a particular part of the body may allow:

Administration of fluids (i.e., heparinized saline, contrast dyes) during an electrophysiology, or related, study;
Fluid sampling during an electrophysiology, or related, study;
Direct blood pressure measurement during an electrophysiology, or related, study;
Angioplasty, angiography, balloon septostomy, balloon sinuplasty, cardiac, catheter ablation;
Draining urine from the urinary bladder as in urinary catheterization, e.g., the intermittent catheters or Foley catheter or even when the urethra is damaged as in suprapubic catheterization;
Drainage of urine from the kidney by percutaneous (through the skin) nephrostomy;
Drainage of fluid collections, e.g. an abdominal abscess;
Drainage of air from around the lung (pigtail catheter);
Administration of intravenous fluids, medication or parenteral nutrition with a peripheral venous catheter;
Direct measurement of blood pressure in an artery or vein;
Direct measurement of intracranial pressure;
Administration of anaesthetic medication into the epidural space, the subarachnoid space, or around a major nerve bundle such as the brachial plexus;
Administration of oxygen, volatile anesthetic agents, and other breathing gases into the lungs using a tracheal tube;
Subcutaneous administration of insulin or other medications, with the use of an infusion set and insulin pump;
Administering drugs or fluids into a large-bore catheter positioned either in a vein near the heart or just inside the atrium;
Measuring pressures in the heart;
Inserting fertilized embryos from in vitro fertilization into the uterus;
Providing quick access to the central circulation of premature infants using an umbilical line;
Attaching catheters to various other devices;
Hemodialysis using a double or triple lumen, external catheter;
Artificial insemination.

Some devices can include multiple lumens each performing a specific function. These lumens can serve as inflation ports, fluid-transfer channels, guidewire access points, or even steering lumens, among others. As such, devices can have one lumen, or can have multiple lumens. For instance, the device can have 1, 2, 3, 4, 5, 6, 7, 8, 9, or 10 or more lumens. The lumens can be a multi-lumen tube (extruded into a single tube), or can be separately bundled inside a device.

The diameter of a lumen in a medical device can range from about 0.1 to about 5 mm. For instance, the diameter of a lumen can range from about 0.001" to about 0.1", or from about 0.01" to about 0.05" internal diameter.

In some aspects, a medical device can further comprise a needle attached to tubing comprising the lumen. The gage of the needle can range from about 50 ga to about 5 ga, from about 40 ga to about 10 ga, or from about 30 ga to about 15 ga.

The length of a lumen of a device can range from about 1 cm to a few meters. For instance, the length of a lumen can range from about 5 cm to about 5 meters, from about 20 cm to about 4 m, from about 50 cm to about 2 m. In some aspects, the length of a lumen can range from about 50 cm to about 150 cm.

In some aspects, the medical device is selected from a Biosense Webster PentaRay, an Abbott Advisor HD Grid, an Abbot BRK Transseptal Needle, a Baylis NRG Transseptal Needle, a Boston Scientific Orion; an Abbott Response with Lumen; a Baylis EPstar; a Phillips Eagle Eye, or an Acutus AcQSpan.

(b) Occluding the Lumen

The method comprises isolating a defined number of one or more occluding test particles and occluding the lumen of a representative device by adhering the one or more particles in the lumen of the representative device. A defined number of particles is an accurate number of isolated particles that can vary depending on the acceptance criteria to be determined for a device. For instance, 1, 2, 3, 4, 5, 6, 7, 8, 9, 10, 20, 30, 40, 50, 60, 70, 80, 90, 100, 500, 1000 or more particles can be isolated for adhering in the lumen of a representative device. In some aspects, a single particle is isolated.

Any method capable of isolating an accurate number of particles can be used in the method, provided the method can isolate a precise number of particles. For instance, the number of particles can be isolated by diluting a solution comprising the one or more particle, and aliquoting a volume of the solution statistically calculated to comprise the desired number of particles. The number of particles can further be confirmed in each aliquot, for instance, under magnification. In some aspects, the beads are suspended in a bead solution and isolated under magnification. The volume of solution into which particles are resuspended can and will vary depending on the device, the size of the lumen of the device, and the number of particles suspended in the bead solution, among other variables. In some aspects, one or more single particles are isolated under magnification into 100 μl of bead solution. In some aspects, the bead solution comprises a surfactant and an adhesive. Surfactants can be as described in Section I(B), and adhesives can be as described in Section I(C).

The bead solution can comprise about 0.001%, 0.005%, 0.01%, 0.05%, 0.1%, 0.5%, 1%, 1.5%, 2%, 2.5%, 3%, 3.5%, 4%, 4.5%, or about 5% adhesive. The bead solution can comprise less than about 0.001%, 0.0055%, 0.01%, 0.05%, 0.1%, 0.5%, 1%, 1.5%, or less than about 2% adhesive. In some aspects, the bead solution comprises less than about 0.01%, 0.05%, 0.1%, 0.5%, or less than about 1% adhesive. In some aspects, the bead solution comprises less than about 0.1%, 0.2%, or less than about 0.3% adhesive. In some aspects, the polymeric adhesive is a polymeric adhesive. In some aspects, the adhesive is a polymeric adhesive, and the solution comprises less than about 0.1%, 0.2%, or less than about 0.3% polymeric adhesive. In one aspect, the polymeric adhesive is an aqueous polymeric adhesive. In some aspects, the adhesive is an aqueous polymeric adhesive, and the solution comprises less than about 0.3%, 0.2%, or less than about 0.1% aqueous polymeric adhesive.

The bead solution can comprise about 00.01%, 0.05%, 0.1%, 0.5%, 1%, 1.5%, 2%, 2.5%, 3%, 3.5%, 4%, 4.5%, 5%, 6%, 7%, 8%, 9%, or less than about 10% surfactant. The bead solution can comprise less than about 0.05%, 0.1%, 0.5%, 1%, 1.5%, 2%, 2.5%, or less than about 3% surfactant. In some aspects, the bead solution comprises less than about 00.01%, 0.05%, 0.1%, 0.5%, 1%, 1.5%, 2%, 2.5%, 3%, 3.5%, 4%, 4.5%, 5%, 6%, 7%, 8%, 9%, or less than about 10% surfactant. The bead solution can comprise less than about 00.05%, 0.1%, 0.5%, 1%, 1.5%, 2%, 2.5%, or less than about 3% surfactant. In some aspects, the bead solution comprises less than about 0.05%, 0.1%, 0.5%, 1%, 1.5%, 2%, 2.5%, or less than about 3% surfactant. In some aspects, the bead solution comprises less than about 0.3%, 0.2%, or less than about 0.1% surfactant.

In some aspects, the bead solution is a buffered bead solution comprising less than about 0.2% aqueous polymeric adhesive and less than 0.5% surfactant. Buffered solutions comprise a buffering agent or a pH modifying agent. Methods of identifying buffering agents to prepare a buffered solution suitable for a bead buffer solution are known in the art and can be determined experimentally. Representative examples of suitable buffering agents include, but are not limited to, phosphates, carbonates, citrates, tris buffers, and buffered saline salts (e.g., Tris buffered saline or phosphate buffered saline). The excipient may also be salts for varying osmolarity. By way of non-limiting example, the pH modifying agent may be sodium carbonate, sodium bicarbonate, sodium citrate, citric acid, or phosphoric acid.

The lumen of the representative device is occluded with the defined number of one or more of the isolated particles. To occlude the lumen, the particles are introduced into the lumen of the representative device and adhered in the lumen. Generally, particles are suspended in a solution comprising an adhesive for attaching particles in the lumen and introduced into the lumen of the representative device. The particles can be allowed to flow toward the middle of the lumen. The solution can then be removed and dried of any residual moisture to remove all fluid to not hinder data collection. The solution can be removed by allowing the solution to evaporate. In some aspects, the solution is oven incubated to remove residual moisture that could confound the data. An oven can be a recirculating air oven. In some aspects, the lumen is dried by incubating the device in a recirculating air oven for about 48 hours at about 65° C.

An inspection method developed using a method of the disclosure can detect particles as small as 50 microns. The method can also detect a wide range of particle quantities, allowing a full scale to be developed by which occlusions (partial or otherwise) could be graded. For instance, an inspection method can be developed to select unoccluded inspected devices, or inspected devices occluded to a level acceptable for the specific device. In some aspects, the representative device is occluded with one occluding particle. In one aspect, the representative device is occluded with 50 microns NIST traceable particle size standard polystyrene beads A. Particles The size of particles suitable for use in the instant disclosure can and will vary depending on the device, the size of the lumen of the device, the method in which the device is intended for use, and the desired level of resolution of the testing method. In general, particles have an accurate validated size distribution and shape. Particle size standards may be used to validate sizing instruments across their dynamic ranges. They are suitable for use in the performance of routine instrument calibration checks and corrections, and in the support of practice standards, such as those published by ISO, ASTM International, CEN, NIST and other organizations. Additionally, the use of reference material permits the standardization of results between runs, instruments and laboratories, and over time. In some aspects, the particles are NIST (National Institute of Standards and Technology) Traceable Size Standards. NIST traceability provides an official, objective third-party comparison of beads to a known standard and maintained by the National Institute of Standards and Technology. The particles can be made of any suitable material, including polystyrene, silica, and glass.

When the device is a medical device, the particle can have a diameter ranging from about 40 nm to 1 μm, from about 1 mm to about 10 μm, or from about 200 μm to about 20 μm. In some aspects, the diameter of particles suitable for use in the disclosure can have a diameter of about 50 μm. In some aspects, the beads are 50 microns NIST traceable particle size standard polystyrene beads.

B. Surfactants

Surfactants can be included in a bead buffer solution to facilitate introduction into a lumen and prevent agglomeration of the particles. The solution can comprise one surfactant or a system of surfactants comprising one or more surfactants.

A variety of surfactants may be included in the surfactant system. Non-limiting examples of suitable nonionic surfactants include sorbitan esters such as sorbitan (Span 20), sorbitan monopalmitate (Span 40), sorbitan monostearate (Span 60), sorbitan monooleate (Span 80), sorbitan sesquioleate (Span 83), sorbitan trioleate (Span 85), sorbitan isostearate (Span 120), or combinations thereof; polyethoxylated sorbitan esters such as polyoxyethylene (20) sorbitan monolaurate (Tween 20), polyoxyethylene (4) sorbitan monolaurate (Tween 21), polyoxyethylene (20) sorbitan monopalmitate (Tween 40), polyoxyethylene (20) sorbitan monostearate (Tween 60), polyoxyethylene (4) sorbitan monostearate (Tween 61), polyoxyethylene (20) sorbitan tristearate (Tween 65), polyoxyethylene (20) sorbitan monooleate (Tween 80), or combinations thereof; polyglycerol esters of fatty acids such as triglycerol monolaurate, triglycerol monooleate, triglycerol monostearate, polyglycerol oleate, polyglycerol, laurate, polyglycerol stearate, polyglycerol polyricinoleate, and so forth; and other nonionic surfactants such as glyceryl monolaurate, glyceryl monooleate, glyceryl monostearate, glycol distearate, glycol stearate, ceteareth-20, cetearyl glycoside, ceteth-2, ceteth-10, ceteth-20, cocamide MEA, isoceteth-20, isosteareth-20, laureth-4, laureth-23, methyl glucose sesquistearate, oleth-2, oleth-10, oleth-20, PEG-100 stearate, PEG-20 almond glycerides, PEG-60 almond glycerides, PEG-20 methyl glucose sesquistearate, PEG-7 hydrogenated castor oil, PEG-25 hydrogenated castor oil, PEG-35 hydrogenated castor oil, PEG-40 hydrogenated castor oil, PEG-60 hydrogenated castor oil, PEG-200 hydrogenated glyceryl palmate, PEG-30 dipolyhydroxystearate, PEG-4 dilaurate, PEG-40 sorbitan peroleate, PEG-7 olivate, PEG-7 glyceryl cocoate, PEG-8 dioleate, PEG-8 laurate, PEG-8 oleate, PEG-80 sorbitan laurate, PEG-40 stearate, propylene glycol isostearate, stearamide MEA, steareth-2, steareth-20, steareth-21, steareth-100, polyoxyethylene (7-8) p-t-octyl phenol (Triton X-114), polyoxyethylene (9-10) p-t-octyl phenol (Triton X-100), polyoxyethylene (9-10) nonylphenol (Triton N-101), polyoxyethylene (9) p-t-octyl phenol (Nonidet P-40), polyoxyethylene (10) cetyl ether (Brij 56), polyoxyethylene (20) cetyl ether (Brij 58), polyoxyethyleneglycol dodecyl ether (Brij 35), copolymers of ethylene oxide and propylene oxide (e.g., Pluronic F-68, Pluronic F-127, etc.), dimethyldecylphosphine oxide (APO-10), dimethyldodecylphosphine oxide (APO-12), cyclohexyl-n-ethyl-β-D-maltoside, cyclohexyl-n-hexyl-β-D-maltoside, cyclohexyl-n-methyl-β-maltoside, n-decanoylsucrose, n-decyl-β-D-glucopyranoside, n-decyl-β-maltopyranoside, n-decyl-β-D-thiomaltoside, n-dodecanoyl sucrose, decaethylene glycol monododecyl ether, N-decanoyl-N-methylglucamine, n-decyl α-D-glucopyranoside, decyl β-D-maltopyranoside, n-dodecanoyl-N-methylglucamide, n-dodecyl α-D-maltoside, n-dodecyl β-D-maltoside, heptane-1,2,3-triol, heptaethylene glycol monodecyl ether, heptaethylene glycol monododecyl ether, heptaethylene glycol monotetradecyl ether, n-hexadecyl β-D-maltoside, hexaethylene glycol monododecyl ether, hexaethylene glycol monohexadecyl ether, hexaethylene glycol monooctadecyl ether, hexaethylene glycol monotetradecyl ether, methyl-6-O—(N-heptylcarbamoyl)-α-D-glucopyranoside, nonaethylene glycol monododecyl ether, N-nonanoyl-N-methylglucamine, N-nonanoyl-N-methylglucamine, octaethylene glycol monodecyl ether, octaethylene glycol monododecyl ether, octaethylene glycol monohexadecyl ether, octaethylene glycol monooctadecyl ether, octaethylene glycol monotetradecyl ether, octyl-β-glucoside, octyl-β-thioglucoside, octyl-β-D-glucopyranoside, octyl-β-D-1-thioglucopyranoside, pentaethylene glycol monodecyl ether, pentaethylene glycol monododecyl ether, pentaethylene glycol monohexadecyl ether, pentaethylene glycol monohexyl ether, pentaethylene glycol monooctadecyl ether, pentaethylene glycol monooctyl ether, polyethylene glycol diglycidyl ether, polyethylene glycol ether, polyoxyethylene (10) tridecyl ether, polyoxyethylene (100) stearate, polyoxyethylene (20) isohexadecyl ether, polyoxyethylene (20) oleyl ether, polyoxyethylene (40) stearate, polyoxyethylene (50) stearate, polyoxyethylene (8) stearate, polyoxyethylene bis(imidazolyl carbonyl), polyoxyethylene (25) propylene glycol stearate, saponin from Quillaja bark, tetradecyl-β-D-maltoside, tetraethylene glycol monodecyl ether, tetraethylene glycol monododecyl ether, tetraethylene glycol monotetradecyl ether, triethylene glycol monodecyl ether, triethylene glycol monododecyl ether, triethylene glycol monohexadecyl ether, triethylene glycol monooctyl ether, triethylene glycol monotetradecyl ether, tyloxapol, n-undecyl β-D-glucopyranoside, octylphenoxypolyethoxyethanol (IGEPAL CA-630), polyoxyethylene (5) nonylphenylether (IGEPAL CO-520), polyoxyethylene (150) dinonylphenyl ether (IGEPAL DM-970), or combinations thereof.

Examples of suitable zwitterionic surfactants include, without limit, lecithins (e.g., a lecithin extracted from soybeans, eggs, milk, marine sources, rapeseed, cottonseed, sunflower, and the like), hydrolyzed lecithins, hydrogenated lecithins, acetylated lecithins, 3-[(3-cholamidopropyl)dimethylammonio]-2-hydroxy-1-propanesulfonate (CHAPSO), 3-[(3-cholamidopropyl)dimethylammonio]-1-propanesulfonate (CHAPS), 3-(4-heptyl)phenyl-3-hydroxypropyl) dimethylammoniopropanesulfonate (C7BzO), 3-(N,N-dimethyloctylammonio) propanesulfonate inner salt (SB3-8), 3-(decyldimethylammonio) propanesulfonate inner salt (SB3-10), 3-(dodecyldimethylammonio) propanesulfonate inner salt (SB3-12), 3-(N,N-dimethyltetradecylammonio) propanesulfonate (SB3-14), 3-(N,N-dimethylpalmitylammonio) propanesulfonate (SB3-16), 3-(N,N-dimethyloctadecylammonio) propanesulfonate (SB3-18), 3-[N,N-dimethyl(3-myristoylaminopropyl)ammonio]propanesulfonate (ASB-14), caprylyl sulfobetaine, capric amidopropyl betaine, capryloamidopropyl betaine, cetyl betaine, cocamidopropyl betaine, C12-14 alkyl dimethyl betaine, cocamidopropyl dimethylaminohydroxypropyl hydrolyzed collagen, N-[3-cocamido)-propyl]-N,N-dimethyl betaine, cocamidopropyl hydroxysultaine, cocamidopropyl sulfobetaine, cocaminobutyric acid, cocaminopropionic acid, cocoamphodipropionic acid, coco-betaine, cocodimethylammonium-3-sulfopropylbetaine, cocoiminodiglycinate, cocoiminodipropionate, coco/oleamidopropyl betaine, cocoyl sarcosinamide DEA, DEA-cocoamphodipropionate, dihydroxyethyl tallow glycinate, dimethicone propyl PG-betaine, N,N-dimethyl-N-lauric acid-amidopropyl-N-(3-sulfopropyl)-ammonium betaine, N,N-dimethyl-N-myristyl-N-(3-sulfopropyl)-ammonium betaine, N,N-dimethyl-N-palmityl-N-(3-sulfopropyl)-ammonium betaine, N,N-dimethyl-N-stearamidopropyl-N-(3-sulfopropyl)-ammonium betaine, N,N-dimethyl-N-stearyl-N-(3-sulfopropyl)-ammonium betaine, N,N-dimethyl-N-tallow-N-(3-sulfopropyl)-ammonium betaine, disodium caproamphodiacetate, disodium caproamphodipropionate, disodium capryloamphodiacetate, disodium capryloamphodipropionate, disodium cocoamphodiacetate, disodium cocoamphodipropionate, disodium isostearoamphodipropionate, disodium laureth-5 carboxyamphodiacetate, disodium lauriminodipropionate, disodium lauroamphodiacetate, disodium lauroamphodipropionate, disodium octyl b-iminodipropionate, disodium oleoamphodiacetate, disodium oleoamphodipropionate, disodium PPG-2-isodeceth-7 carboxyamphodiacetate, disodium stearoamphodiacetate, N,N-distearyl-N-methyl-N-(3-sulfopropyl)-ammonium betaine, ethylhexyl dipropionate, ethyl hydroxymethyl oleyl oxazoline, ethyl PEG-15 cocamine sulfate, isostearamidopropyl betaine, lauramidopropyl betaine, lauramidopropyl dimethyl betaine, lauraminopropionic acid, lauroamphodipropionic acid, lauroyl lysine, lauryl betaine, lauryl hydroxysultaine, lauryl sultaine; linoleamidopropyl betaine, lysolecithin, myristamidopropyl betaine, octyl dipropionate, octyliminodipropionate, oleamidopropyl betaine, oleyl betaine, 4,4(5H)-oxazoledimethanol, palmitamidopropyl betaine, palmitamine oxide, ricinoleamidopropyl betaine, ricinoleamidopropyl betaine/IPDI copolymer, sesamidopropyl betaine, sodium C12-15 alkoxypropyl iminodipropionate, sodium caproamphoacetate, sodium capryloamphoacetate, sodium capryloamphohydroxypropyl sulfonate, sodium capryloamphopropionate, sodium cocaminopropionate, sodium cocoamphoacetate, sodium cocoamphohydroxypropyl sulfonate, sodium cocoamphopropionate, sodium dicarboxyethyl cocophosphoethyl imidazoline, sodium isostearoamphopropionate, sodium lauriminodipropionate, sodium lauroamphoacetate, sodium oleoamphohydroxypropylsulfonate, sodium oleoamphopropionate, sodium stearoamphoacetate, sodium tallamphopropionate, soyamidopropyl betaine, stearyl betaine, trisodium lauroampho PG-acetate phosphate chloride, undecylenamidopropyl betaine, or combinations thereof.

In some aspects, the surfactant is Triton™ X-100, Tween® 20, or combinations thereof.

C. Adhesive

The particles are adhered in the lumen using an aqueous polymeric adhesive. In some aspects, a suitable adhesive is a polymeric adhesive. Non-limiting examples of suitable polymeric glues include epoxy resins, epoxy putty, ethylene-vinyl acetate (a hot-melt glue), phenol formaldehyde resin, polyamide, polyester resins, polyethylene (a hot-melt glue), polypropylene, polysulfides, polyurethane, polyvinyl acetate (PVA), polyvinyl alcohol, polyvinyl chloride (PVC), polyvinyl chloride emulsion (PVCE), polyvinylpyrrolidone (PVP), rubber cement, silicones, silyl modified polymers, and styrene acrylic copolymer. A combination of more than one glue can also be used in a bead solution. In some aspects, the adhesive is a water-based adhesive such as PVP. It will be recognized that the concentration of the glue in a bead solution can and will vary depending on the glue, the particle material, and material of the lumen. However, any concentration of glue sufficient to adhere and maintain the particles in the lumen can be used, and can be determined experimentally.

(c) Mass Flow Measurement

The method comprises obtaining a mass flow measurement for a representative device occluded as described in Section I(b). During mass flow measurement, a lumen can be charged to a predetermined pressure with air, and then air can be delivered through the lumen at a sufficient rate to maintain that pressure, thereby obtaining the mass flow rate. The mass flow rate can be the standard cubic centimeters per minute (sccm). One sccm indicates the mass flow rate of one cubic centimeter per minute of a fluid.

Impacted by the cross-sectional area of the blockage, a fully occluded device will allow little to no quantity ($\Delta Q=0$) of gas to exit the lumen, thereby requiring little to no additional flow of air to maintain the charge pressure. Non-occluded devices will allow full and rapid flow of gas exiting the lumen, as there is no impedance other than that provided by the properties of the lumen itself (i.e., material, geometry, surface finish, etc.). This will require a much higher flow of air to maintain the charge pressure. Partially occluded devices will impede this flow to the degree by which they are obstructed as defined in the standard mass flow equation below, requiring a flow of air between that of the fully and non-occluded devices.

$$\Delta Q = \frac{\pi \Delta P d^4}{128 \, \mu l}$$

As such, any mass flow measurement instrument can be used in this method, provided the device can accommodate a device of interest, and provide the desired pressure. For instance, the mass flow measuring device is able to accommodate a device comprising a lumen having the correct lumen size, and capable of providing an unimpeded flow rate of any subject device sufficient for the development of an inspection method. When the device is a medical device comprising a microlumen, the mass flow measurement instrument can be the Sentinel Blackbelt Test System from Cincinnati Test Systems (CTS).

It will be understood that flow characteristics differ between different types of devices, and can be affected by, among other variables, the material in the lumen, lumen diameter and architecture, usable length, curves or device-specific parts attached along the fluid flow of the lumen. Therefore, characterization of each device is required in the development of device-specific test acceptance criteria. The mass flow rate for each device can be determined experimentally by measuring the mass flow through an unoccluded device. Similarly, a predetermined pressure to which a lumen is charged, and a preset period of time for which the flow of air is maintained also depend on the device, the lumen of the device, and the mass flow measuring device among other variables, and can be determined experimentally.

(d) Calculating a Test Limit Value

The method comprises calculating an upper test limit mass flow rate for a device of interest. An upper test limit mass flow rate can be the upper boundary of a probability plot at 95/85 confidence interval or higher. For instance, upper test limit mass flow rate can be the upper boundary of a probability plot at a confidence interval of 95/85, 95/85, 95/85, 95/85, 95/85, 95/90, 95/90, 95/90, 95/90, 95/90, 95/90, 95/90, 95/90, 95/90, 95/90 or above. In some aspects, the test limit can be about 95/99.82.

In some aspects, the upper test limit value is calculated by preparing a probability distribution plot for flow rates from more than one representative device occluded with a defined number of particles. The upper test limit mass flow rate is the acceptance criteria, and an inspected device is occluded if a mass flow measurement in the inspected device is equal to or lower than the acceptance criteria, and an inspected device is unoccluded if the mass flow measurement in the inspected device is higher than the acceptance criteria.

Figure 4:
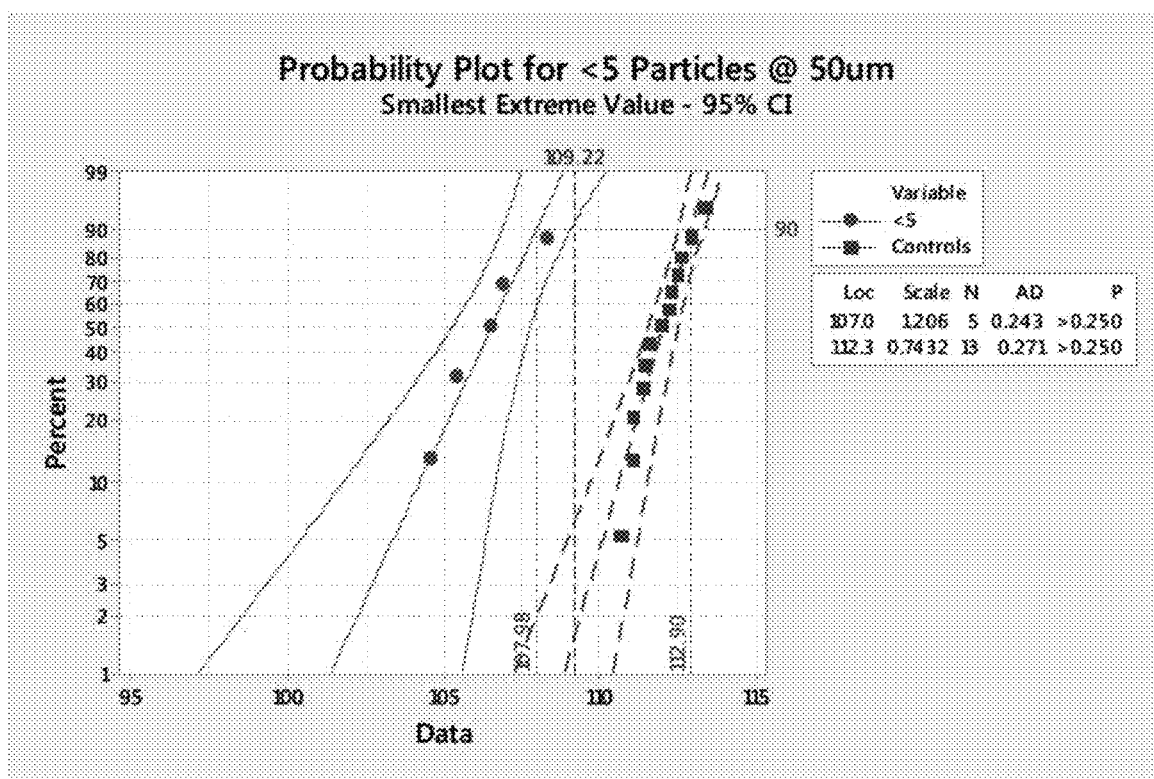
FIG. 4 is a probability distribution plot for flow rates from devices containing 5 or fewer particles, and the control devices. The 95/90 values are shown, along with the calculated test limit value (109.22 sccm; dashed vertical line at 109.22 sccm) incorporating system error of 0.5% of full scale (1.24 sccm).

In example 1, a probability distribution plot for flow rates from Biosense Webster PentaRay EP catheters containing 5 or fewer particles and from control catheters is shown in FIG. 4. The upper test limit value at 95/90 confidence interval for the PentaRay catheter was calculated to be 109.22 sccm, and is shown in FIG. 4 as a dashed vertical line. In some aspects, the device is Biosense Webster PentaRay EP catheter, and the acceptance criteria is 109.23 sccm. In other aspects, the device is Abbott (St. Jude Medical) Advisor HD Grid mapping catheters, and the acceptance criteria is 157.32 sccm. In yet other aspects, the device is St. Jude Medical BRK Transseptal Needle having a length of 71 cm, and the acceptance criteria is 175.8 sccm. In other aspects, the device is St. Jude Medical BRK Transseptal Needle having a length of 89 cm, and the acceptance criteria is 161.1 sccm. In additional aspects, the device is St. Jude Medical BRK Transseptal Needle having a length of 98 cm, and the acceptance criteria is 154.3 sccm. In other aspects, the device is St. Jude Medical BRK Transseptal Needle having a length of 89 cm, and the acceptance criteria is 161.1 sccm.

As explained above in Section I(c), flow rate is device-specific. Therefore, an upper test limit mass flow rate can be determined for each type of device.

II. Inspection Methods

In one aspect, the present disclosure provides an inspection method for identification of occluding particles in a lumen of an inspected device. The method comprises determining acceptance criteria for identification of occluding particles in the lumen of the inspected device. Acceptance criteria can be determined as described in Section I above.

Once the acceptance criteria for the device is determined, a mass flow measurement is obtained for an inspected device. The mass flow measurement of the inspected device is obtained and compared to the acceptance criteria. The mass flow measurement of the inspected device can be obtained as described in Section I(b) and, if the mass flow measurement of the inspected device is equal to or lower than the test acceptance criteria determined, the inspected device is rejected as comprising an occlusion. The inspected device is accepted if the measured mass flow of the inspected devise is higher than the test acceptance criteria for the device.

III. Computer-Implemented Methods and Systems

In one aspect, the present disclosure provides a system for identification of an occluding particle in an inspected device. The system comprises a mass flow measurement instrument for obtaining a mass flow measurement for the inspected device. The system also comprises a computer system having at least one processor and associated memory comprising acceptance criteria for identification of occluding particles in a lumen of the inspected device and instructions which, when executed by the at least one processor, cause the at least one processor to receive the mass flow measurement and compare the mass flow measurement for the inspected device to the acceptance criteria. The processor also outputs inspection results for identifying an occluded inspected device, wherein the inspected device is occluded if a mass flow measurement in the inspected device is equal to or lower than the acceptance criteria, and the inspected device is unoccluded if the mass flow measurement in the inspected device is higher than the acceptance criteria.

In another aspect, the present disclosure provides a system for determining acceptance criteria for identification of occluding particles in a lumen of a device. The system comprises a mass flow measurement instrument for obtaining a mass flow measurement of a representative device. The system further comprises a computer system having at least one processor and associated memory comprising instructions for calculating an upper test limit mass flow rate for an occluded representative device and instructions which, when executed by at least one processor, cause the at least one processor to receive mass flow measurement of the occluded devices and calculate an upper test limit mass flow rate for the occluded devices. The computer system also outputs the upper test limit mass flow, wherein the upper test limit mass flow rate is the acceptance criteria, and wherein an inspected device is occluded if a mass flow measurement in the inspected device is equal to or lower than the acceptance criteria, and the inspected device is unoccluded if the mass flow measurement in the inspected device is higher than the acceptance criteria.

In one aspect, the present disclosure provides at least one non-transitory computer readable medium storing instructions which, when executed by at least one processor, cause the at least one processor to receive a mass flow measurement of occluded devices and calculate an upper test limit mass flow rate for the occluded devices. The instructions also cause the at least one processor to output test results for accepting or rejecting an inspected device, wherein an inspected device is occluded if the mass flow measurement in the inspected device is equal to or lower than the acceptance criteria, and the inspected device is unoccluded if the mass flow measurement in the inspected device is higher than the acceptance criteria.

In yet another aspect, the present disclosure provides at least one non-transitory computer readable medium storing instructions which, when executed by the at least one processor, cause the at least one processor to receive a mass flow measurement of an inspected device and compare the mass flow measurement for the inspected device to the acceptance criteria. The instructions also cause the at least one processor to output test results for accepting or rejecting the device, wherein an inspected device is occluded if the mass flow measurement in the inspected device is equal to or lower than the acceptance criteria, and the inspected device is unoccluded if the mass flow measurement in the inspected device is higher than the acceptance criteria.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

Methods according to the above can be implemented using computer-executable instructions that are stored or otherwise available from computer-readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

As various changes could be made in the above-described methods without departing from the scope of the invention, it is intended that all matter contained in the above description and in the examples given below, shall be interpreted as illustrative and not in a limiting sense.

As used herein, the term "clinically relevant" refers to a level of particles that may be capable of increasing patient embolic risk.

As used herein, the term "occluded device" refers to a device comprising a lumen and having a lumen occluded by one or more occluding particles.

As used herein, the term "unoccluded device" refers to a device comprising a lumen and having a lumen clear of any occluding particles.

As used herein, the term "representative device" refers to a device used to determine acceptance criteria for an inspected device.

As used herein, an "inspected device" refers to a device having undergone a mass flow measurement for use in a method or system for identifying occluding particles in the lumen of the device.

As used herein, the term "device," when not qualified by the terms "inspected" or "representative", refers to the device for which acceptance criteria are developed, and which undergoes testing for identification of occluding particles in a lumen of the device.

EXAMPLES

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

The publications discussed throughout are provided solely for their disclosure before the filing date of the present application. Nothing herein is to be construed as an admission that the invention is not entitled to antedate such disclosure by virtue of prior invention.

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1. Development of Mass Flow Method of Identification of Occluding Particles in Microlumens An in-process inspection testing method capable of detecting and rejecting devices with microlumens containing unacceptable levels of clinically relevant particles is presented herein.

By adapting current leak testing technology, validated for use in nearly every field, including medical, we have developed a mass flow inspection test that is capable of identifying a single small particle within a microlumen. Further, our investigation also showed that this method could repeatedly identify a wide range of particle quantities, allowing a full scale to be developed by which occlusions (partial or otherwise) could be graded. This test method is intended to create a new standard by which manufacturers of medical devices containing small lumens should consider when attempting to mitigate periprocedural patient risk.

Introduction

Performed to diagnose and treat most arrythmias, an EP study utilizes specialized catheters, introducers, and other complex technologies. These devices are most often inserted via venous (femoral) access and delivered to the right atrium, with a transseptal puncture providing access to left-sided anatomy as necessary. Most studies are routine, completed in a few hours, and the patient can be expected to resume normal daily activities within just a few days. However, with an elementary understanding of anatomy, concern arises that devices placed within cardiac chambers could release potentially embolic particulates. Those discharged into the right side of the heart could occlude pulmonary arterioles (average diameter <300 micron) if large enough, potentially resulting in a pulmonary embolism (PE). Left-sided studies could direct emboli to the brain, potentially resulting in a CVA. Occlusion of penetrating arterioles (average diameter <100 micron) is of greatest concern, inducing more traumatic neuropathy.

A contributing factor to these complications results from potentially embolic particulates either on, in, or created by, a device, fluid, or other object introduced into the patient. The consequences of particles delivered into the bloodstream have long been understood. But, while catheters have been used for EP studies for decades, there exists no single, well-defined standard for particulates on or in an EP catheter, or related, by which manufacturers of such devices must adhere. Many default to those drafted by the United States Pharmacopeia (USP), particularly the direction found in General Chapter <1> Injections and Implanted Drug Products. This chapter focuses on parenternal drug products that are injected or implanted into the body. It further points to other chapters that define additional testing requirements unique to the many different materials considered. The chapter commonly referenced by catheter manufacturers when discussing particulate acceptance criteria is <788> Particulate Matter in Injections. This chapter defines acceptable particulate sizes and quantities in injectables, and the test methods used to characterize them. Here, acceptance criteria focus on larger amounts (600 or 6000) of smaller particulates (25 or 10 micron, respectively). The clinical concern is that patients often receive multiple injections of various required solutions during their care. It has been estimated that a patient in intensive care is injected with as many as a million particles larger than 2 micron every day of their stay. While lesser amounts of smaller particles may not be acutely traumatic, cumulative doses of smaller particulates has proven deleterious. For example, parenternal nutrition solutions have been shown in the past to include nearly 40,000 particles upwards of 100 micron each in daily feedings, with little to no acute risk. However, prolonged administration allows for the accumulation of fatal quantities of particles. Because of this, minimizing the quantity of smaller particles in each injection, either via implementation of inline filters and/or improved manufacturing techniques, will reduce the overall load a patient experiences, abating risk of further embolic complication.

Additional governance is provided by USP regarding perfusion scintigraphy studies, recommending the majority of particulates involved be around 90 micron in diameter (ranging from 20-150 micron), with none larger than 150 micron. It has been shown that smaller particles (<40 micron) may pass through the vasculature of interest and travel to, and become lodged in, unintended sites potentially leading to delayed disfunction after a critical load has been administered, while larger particles (>200 micron) may block arteries and arterioles, resulting in acute focal defects.

Both the Association for the Advancement of Medical Instrumentation (AAMI) and the Food and Drug Administration have released several guiding documents, such as TIR42 (AAMI) and "Guidance for Coronary, Peripheral, and Neurovascular Guidewires" (FDA), among others. These are similar to USP<788> in that they recommend the characterization of certain sizes of particulates that may originate from the medical devices each is focused on, but stop short of defining quantity and size acceptance criteria. This is mostly due to the fact that there is an understandable lack of research involving human subjects given the ethical concerns involved. These documents instead rely on the many related studies employing animal models. While direct correlation is confounded by differences in anatomy, basic principles apply and are intended to aid each manufacturer in defining their own acceptance criteria.

In addition to device-attributed particulates discharged into the vasculature, there is also a concern about potentially embolic-free circulating particulates created during an EP study, especially those procedures involving ablation of intracardiac surfaces. Several studies have identified asymptomatic cerebral lesions via MRI following ablation procedures, leading to a presumed direct correlation between ablation procedures and the production of emboli. A recent pair of studies, sponsored by Medtronic, considered the effect of microembolic materials (either air bubbles or pulverized dried blood) created during ablation in the left atrial chamber on canine and porcine models.

The first study investigated the production of microbubbles and embolic particulates during pulmonary vein (PV) ablation in porcine subjects using two specific catheters (Biosense Webster and Medtronic). In this study, microbubbles and coagulum (averaging 225-250 micron depending on the catheter used) were identified and attributed to the use of the devices, but no evidence of acute cerebral lesions was observed in any of the six participant animals. 73 micron extracorpeal filters were used to collect debris, allowing all smaller debris to continue circulation. In two of the animals, renal arterial occlusion was present with subsequent tubular necrosis, but no other lesions or dysfunction was reported elsewhere.

In the second study, over 4000 particulates or a quantity of microbubbles were injected into a canine subject in four doses (4 injections of >1000 particles, or up to 4 injections of 0.5 mL of microbubbles). Several ranges of sizes were considered, from 75-250 micron to 90-600 micron. The effects of introducing single particles or microbubbles of any size were not studied. Nor were the effects after introducing a quantity of particles of a single size. The location of the injection (vertebral vs carotid sinus) and the size of the particulates directly correlated with increased severity of the outcome.

In both studies, as in several others before and since, a significant load (quantity $10^3$-$10^6$) of larger embolic (>>>50 micron) particles were required to cause injury. Studies on atheroemboli to the brain have shown a remarkable acute tolerance of considerably large emboli (50-300 micron) by the cerebral vasculature, likely due to redundant blood supplies caused by arterial anastomoses and arteriovenous shunts. Considering the other end of the spectrum, an oft-cited work by Heistad, et al., studied the injection of nearly 30,000 smaller beads (15 micron) into a dog model. He repeated these injections 25 times, observing no ill effects or neurologic deficits. However, when he injected a similar quantity of 50 micron beads, altered blood flow was observed after a single dose. Together, this reinforces the earlier conclusion that fewer larger particles can be more harmful than an even greater quantity of smaller particles, and that multiple (>$10^3$) particles in the arteriole size range and smaller are required to induce significant injury.

Manufacturers of products used during EP studies have a shared goal to reduce periprocedural patient injury, especially emboli. As such, good manufacturing practices include methods that specifically minimize and/or remove particulates on or in these products. Further, adequate inline inspection should be performed on each device, rejecting those that contain an unacceptable level of particulates. This is a relatively routine task when patient contacting surfaces are visible on the exterior of the device. Low level magnification allows for detection of particles that could be of concern. Unfortunately, this becomes significantly more complicated with devices that contain lumens, especially when they are inaccessible. Visualization solutions exist for macrolumens, but more specialized testing must be developed and validated for other microlumen products. The testing methods that follow discuss a novel approach to identifying clinically relevant levels of particulates within microlumens or EP devices.

Test Method Development

The test to identify occluded devices relies on standard principles of fluid dynamics and physics where:

| Flow(Q)= | Quantity (q) | Pressure(P)= | Force(F) |
|---|---|---|---|
| | Time (t) | | Area (A) |

A lumen can be charged to a certain pressure with air, and then air can be delivered through the lumen at a rate required to maintain that pressure. Impacted by the cross-sectional area of the blockage, a fully occluded device will allow little to no quantity ($\Delta AQ=0$) of gas to exit the lumen, thereby requiring little to no additional flow of air to maintain the charge pressure. Non-occluded devices will allow full and rapid flow of gas exiting the lumen, as there is no impedance other than that provided by the properties of the lumen itself (i.e., material, geometry, surface finish, etc.). This will require a much higher flow of air to maintain the charge pressure (FIG. 1). Partially occluded devices will impede this flow to the degree by which they are obstructed as defined in the standard mass flow equation below, requiring a flow of air between that required for the fully and non-occluded devices.

This testing is commonly referred to as mass flow testing. It is ideally suited for use with microlumens because it is capable of grading the degree of blockage, which is necessary for detecting partial occlusions caused by small particles. Other pressure-based methods are designed for detecting only higher levels of occlusion, so are poorly suited for this application. The addition of a mass flow transducer along with the pressure sensor provides the added sensitivity necessary to ensure that only acceptable levels of particles remain on a device.

The mass flow testing was conducted using a Cincinnati Test Systems (CTS) Sentinel Blackbelt Test System. It utilizes clean, dry, pressurized air to create positive pressure inside a device and provides constant timed flow, which is then sensed by mass flow transducers accurate to 0.5% of full scale (248 sccm scale=±1.2 sccm error). Data is displayed at a 0.00001 resolution.

Development of this test method involved an assessment of the ability of to distinguish between different sized particles as well as different quantities of similar sized particles. This established both a sensitivity range and determined if the instrument was capable of detecting a particle smaller than that deemed clinically relevant. Developing the method to detect particle smaller than that deemed clinically relevant provides for a safety factor, rejecting devices containing such small particles. Based on the review of literature, and discussions with the FDA, a particle size of 50 micron was chosen for establishing acceptance criteria.

Figure 8:
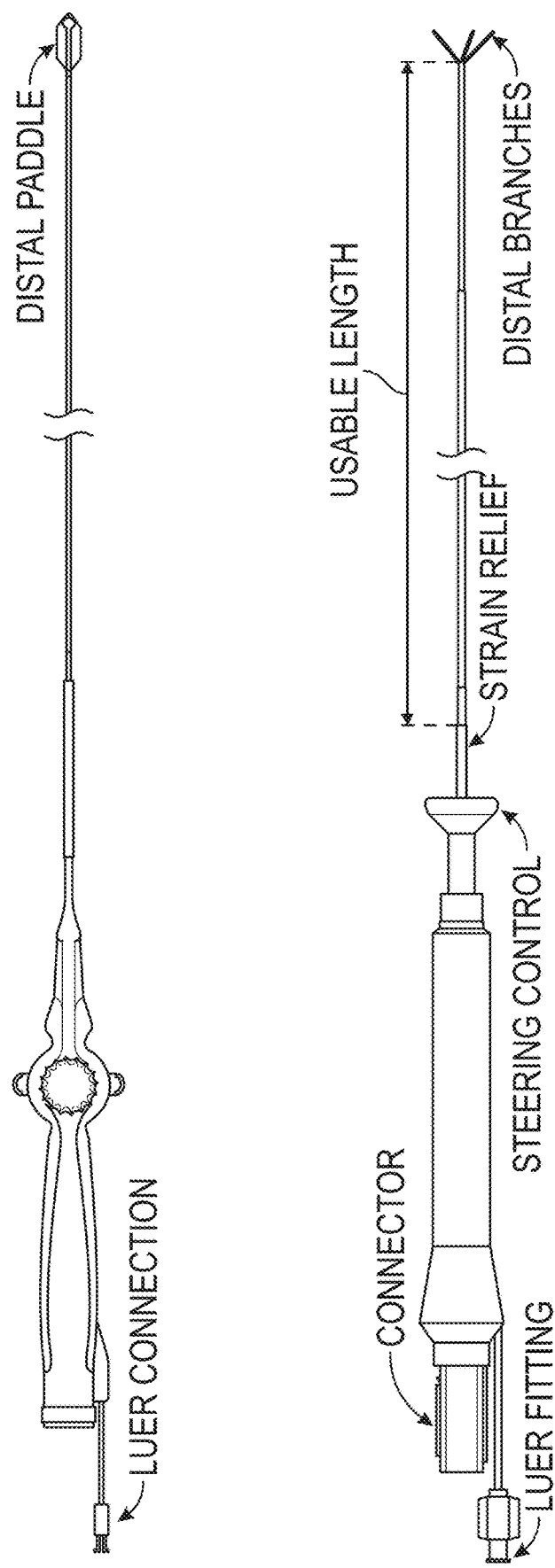
FIG. 8. Design characteristics of the Advisor HD Grid (top) and PentaRay (bottom) catheters.
Figure 9A:
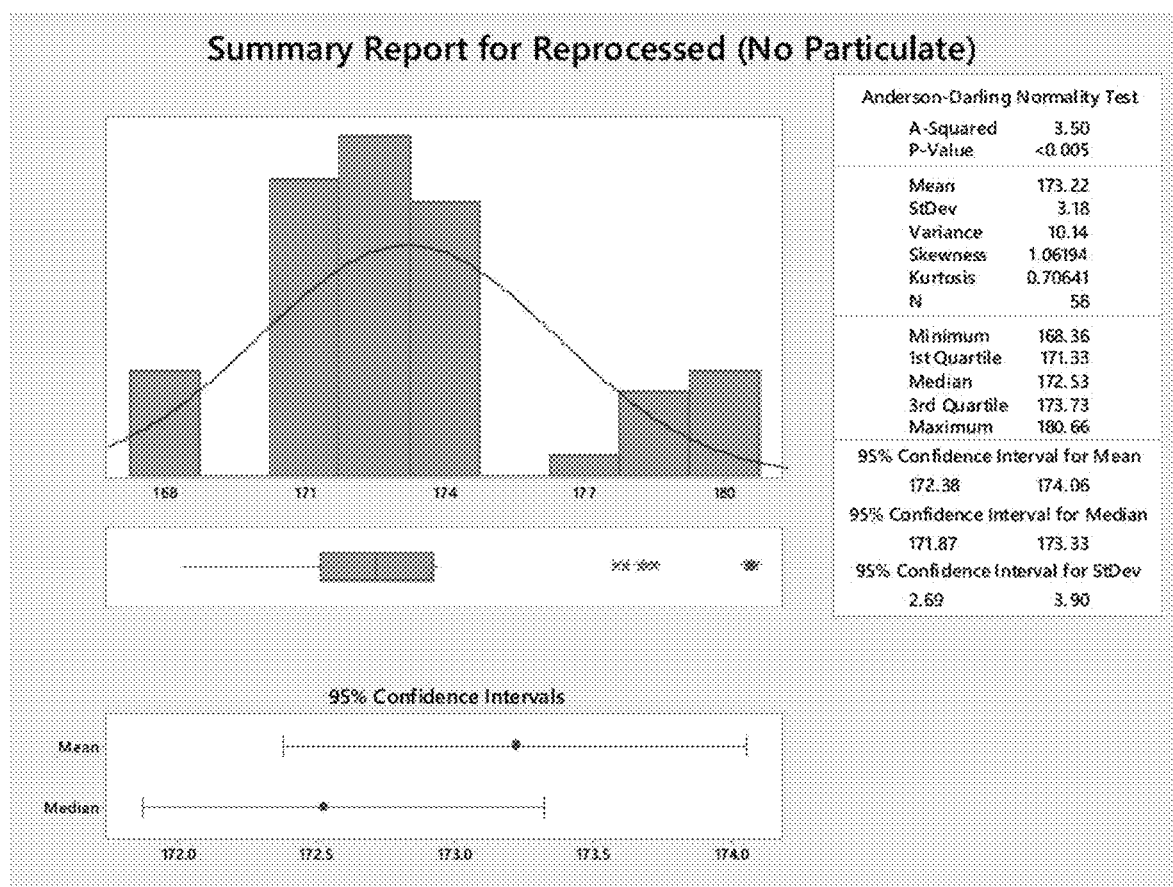
FIG. 9A depicts a summary report for reprocessed (No Particulate) devices.
Figure 9B:
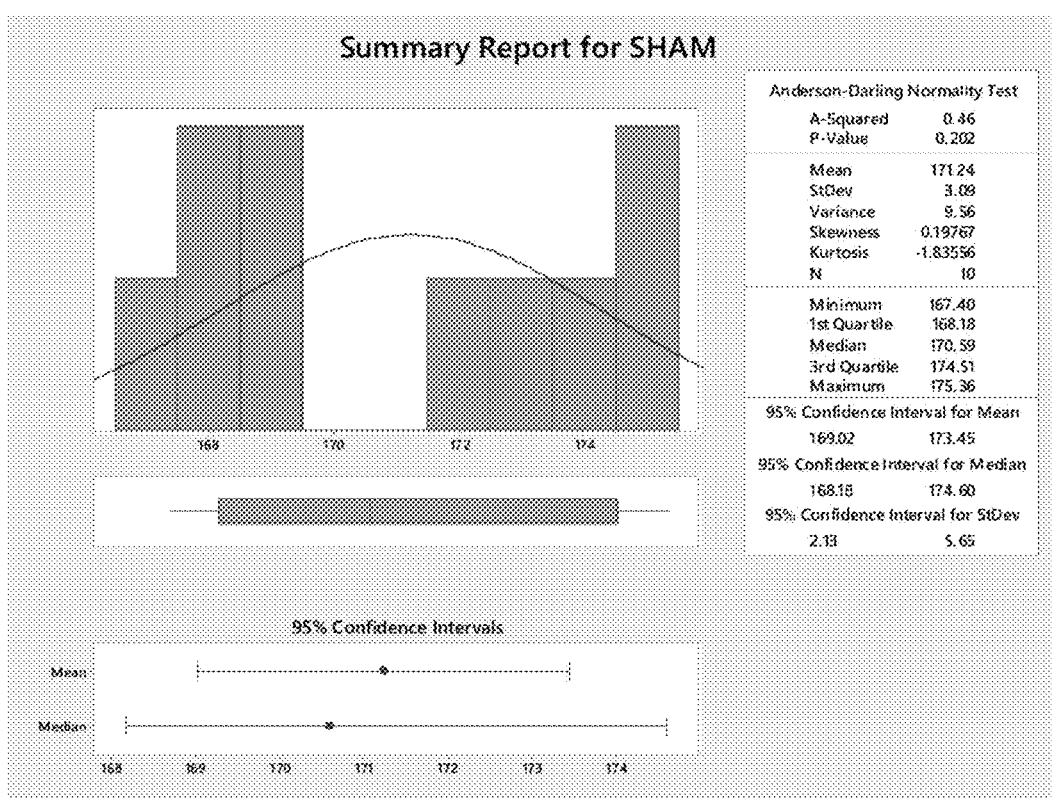
FIG. 9B depicts a summary report for reprocessed (+Particulate) devices. Occluded devices were inoculated with a single 50 µm bead.
Figure 9C:
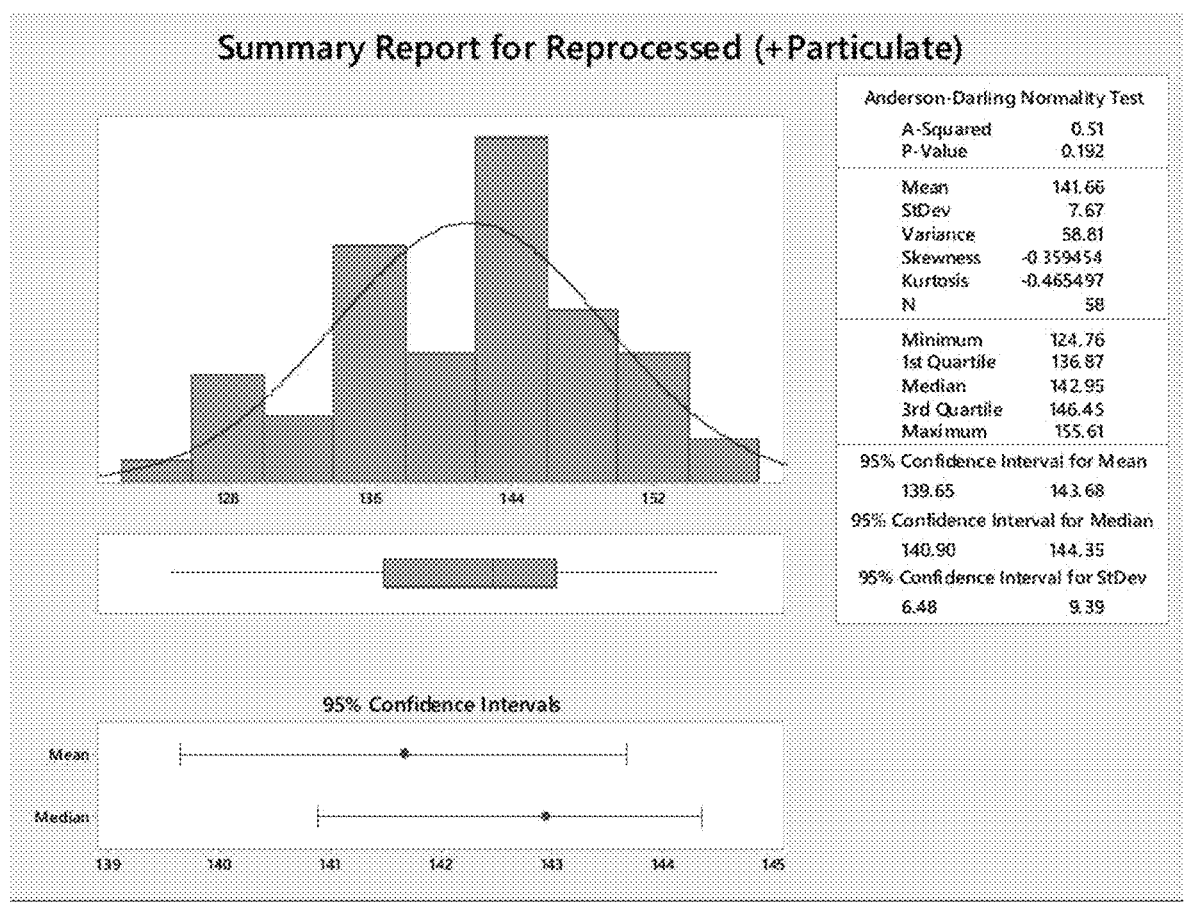
FIG. 9C depicts a summary report for Sham devices. Sham devices were inoculated with the bead buffer (carrier) solution only.
Figure 10:
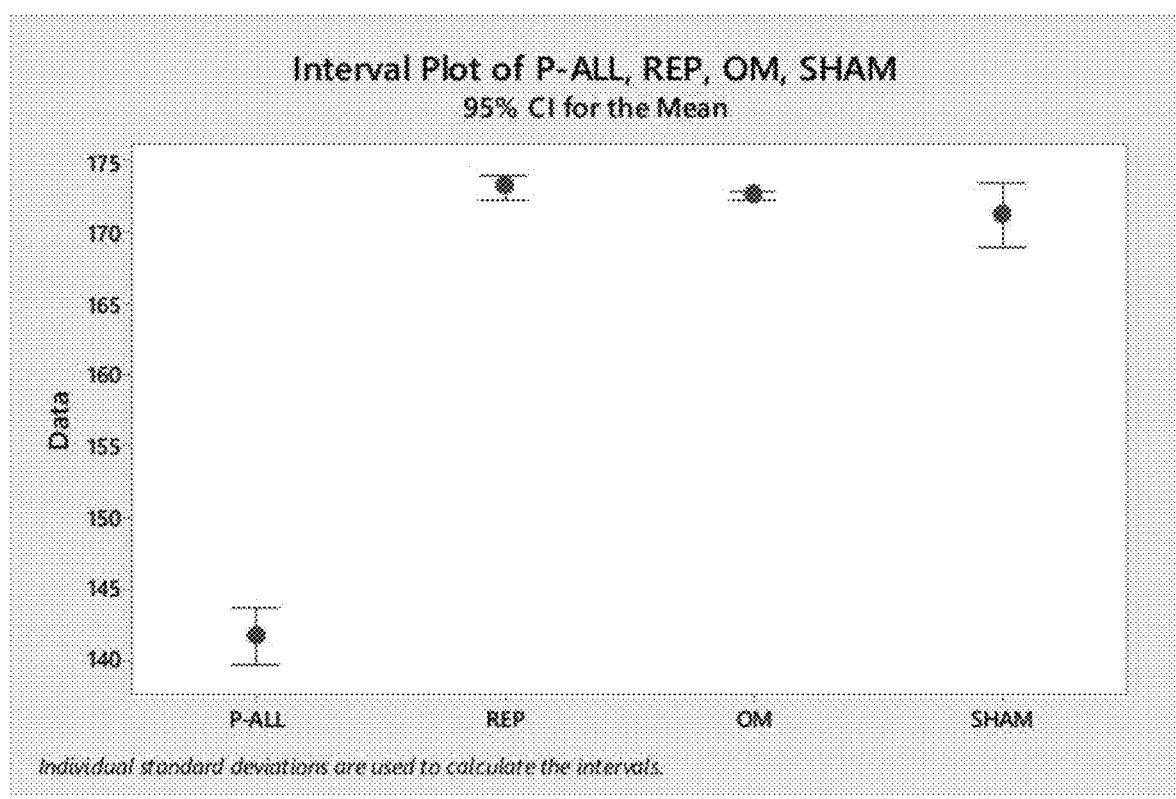
FIG. 10 depicts an interval plot displaying minimal differences in flow between non-occluded OM, Reprocessed, and Sham inoculated devices, but a significant drop in flow between all of those sample sets and the devices occluded with a single 50 µm bead.
Figure 11:
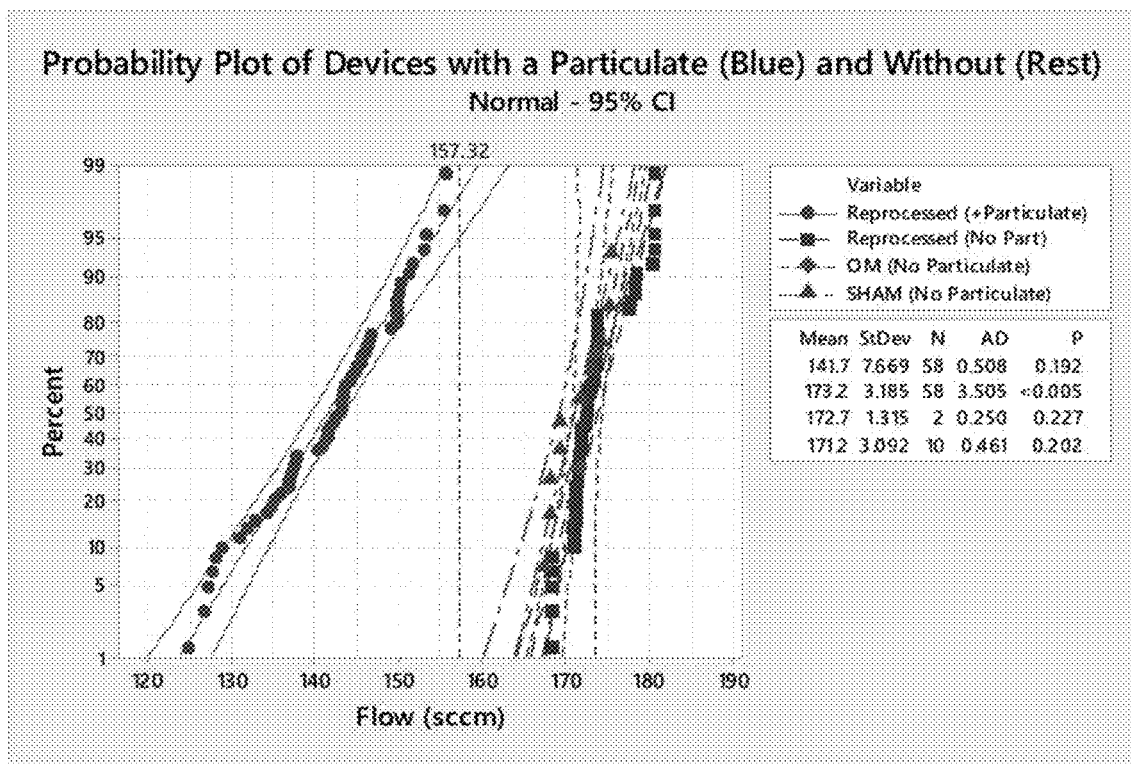
FIG. 11 depicts the upper boundary of the probability plot at 95/95 confidence interval for the devices occluded with a single 50 µm bead is 157.32 sccm. It is also noted that the OM devices perform in a similar manner to reprocessed devices (both without particulates). The sham readings display no significant impact of the carrier fluid on the flow rate (post incubation).
Figure 12:
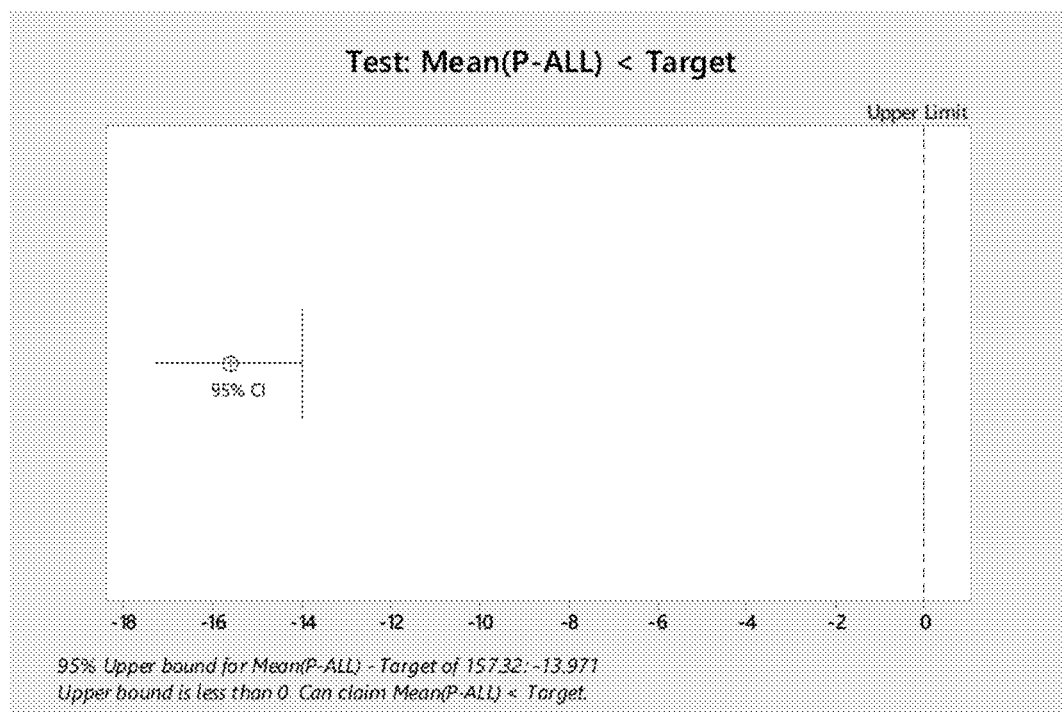
FIG. 12 depicts an equivalence test showing a significant difference between the mean of all occluded samples and the acceptance criteria of 157.32 sccm, and also between the mean of all reprocessed (non-occluded) samples and the acceptance criteria.
Figure 13:
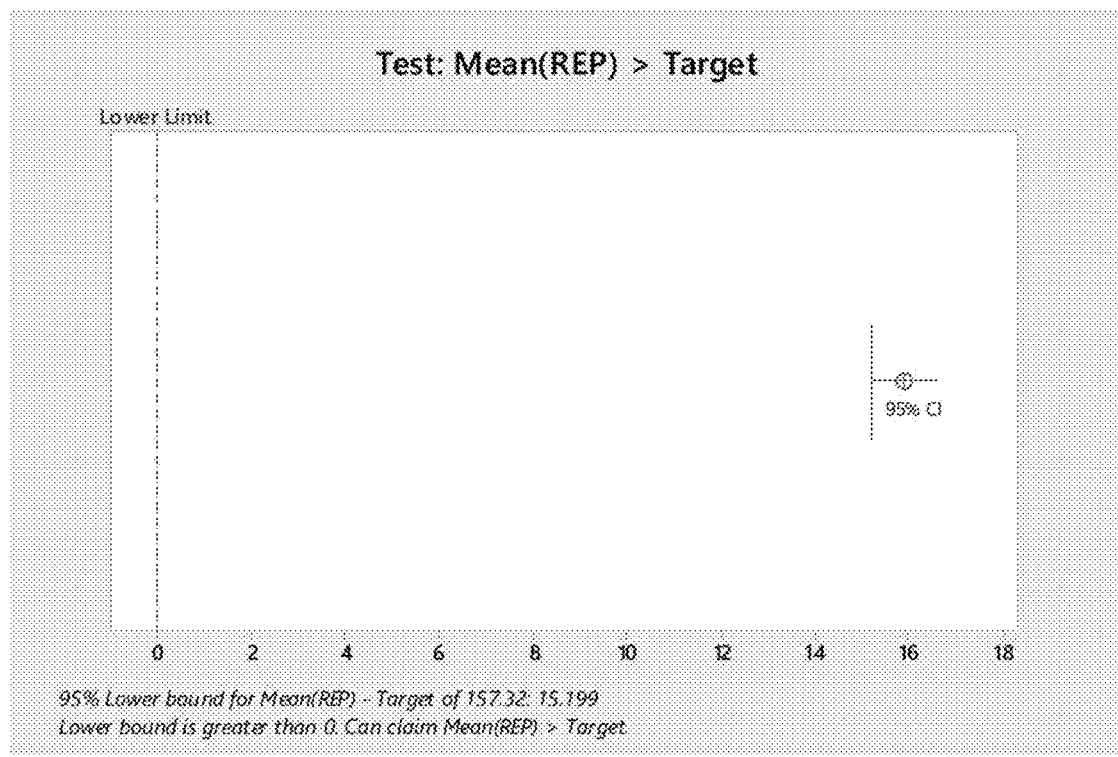
FIG. 13 depicts a distribution plot, which assumes an infinite sample set, suggests the 95/95 acceptance criteria of 157.32 sccm approaches 95/98.
Figure 14A:
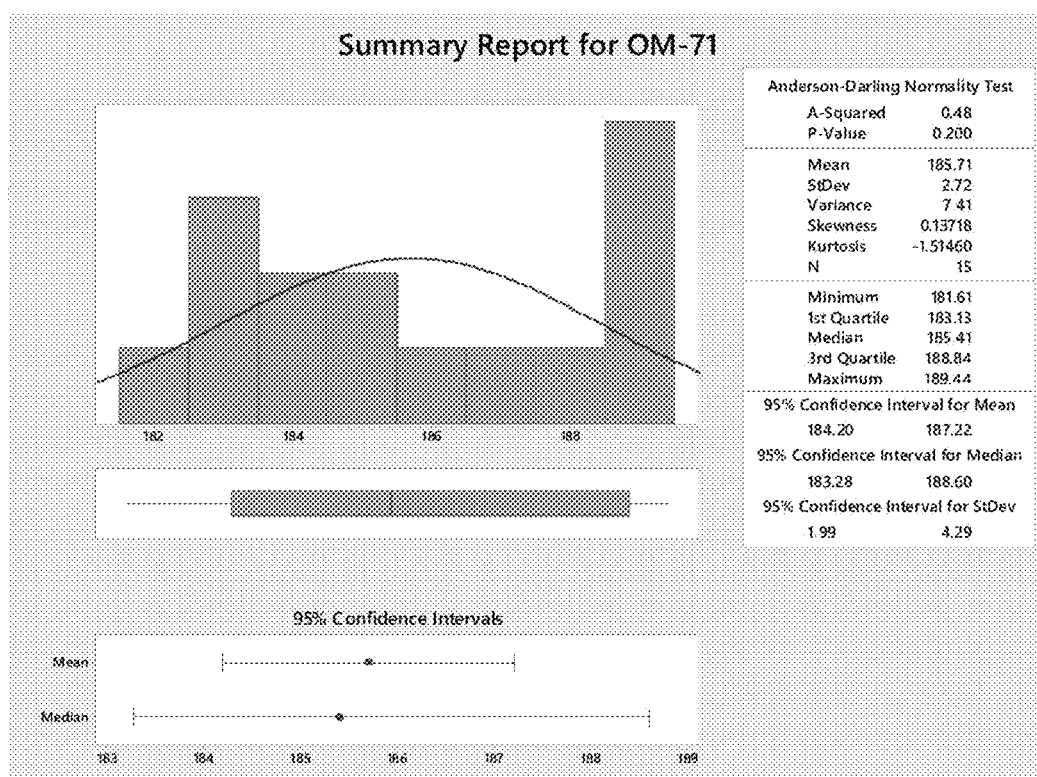
FIG. 14A depicts a summary report for reprocessed (No Particulate) devices.
Figure 14B:
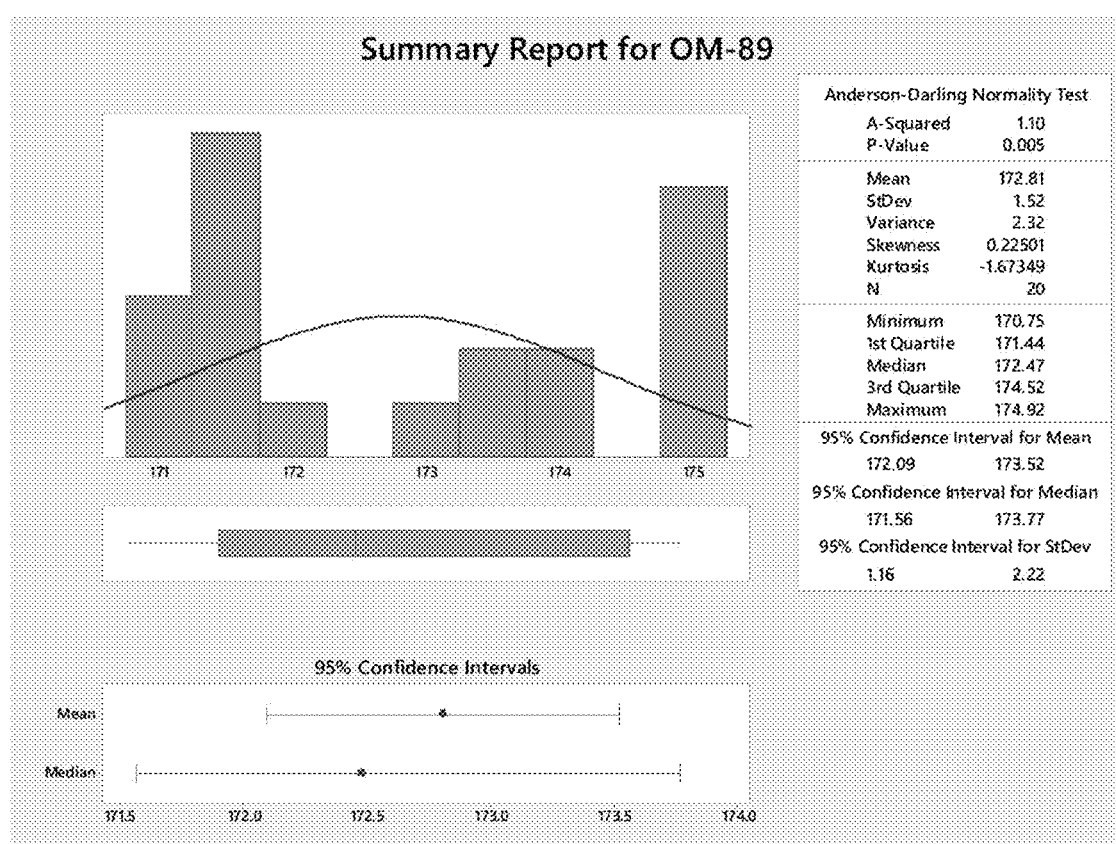
FIG. 14B depicts a summary report for reprocessed (+Particulate) devices. Occluded devices were inoculated with a single 50 µm bead.
Figure 14C:
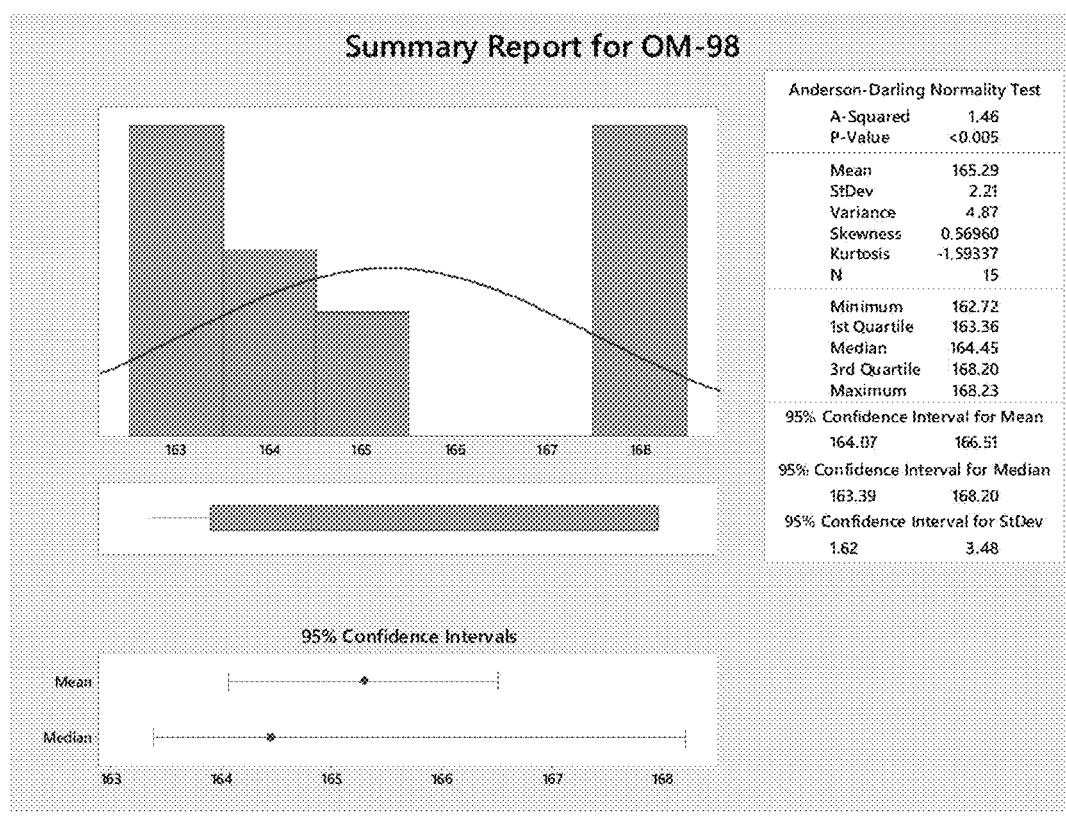
FIG. 14C depicts a summary report for Sham devices. Sham devices were inoculated with the bead buffer (carrier) solution only.
Figure 15:
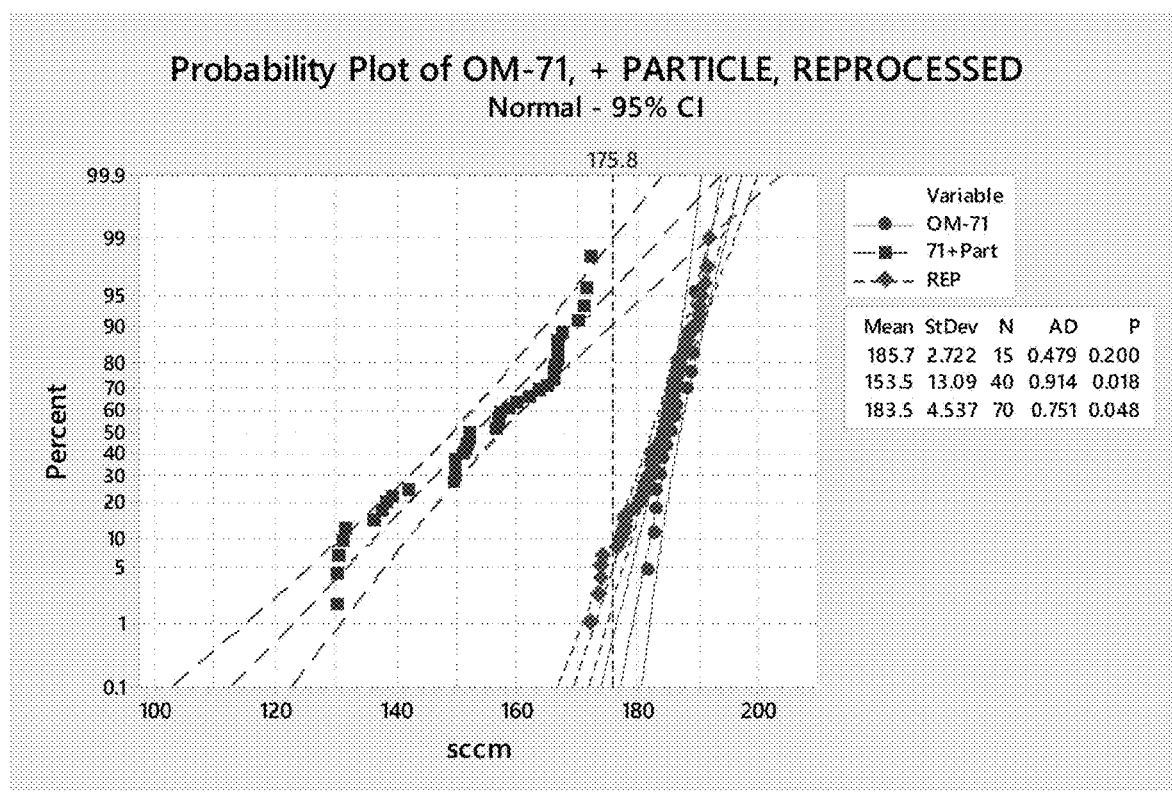
FIG. 15 shows the mass flow rates for 71 cm OM and Reprocessed devices without an occluding particulate and reprocessed devices inoculated with an occluding particulate. The +Particulate 95/90 upper test limit (UTL) flow rate is shown, defining the acceptance criteria for 71 cm needles.
Figure 16:
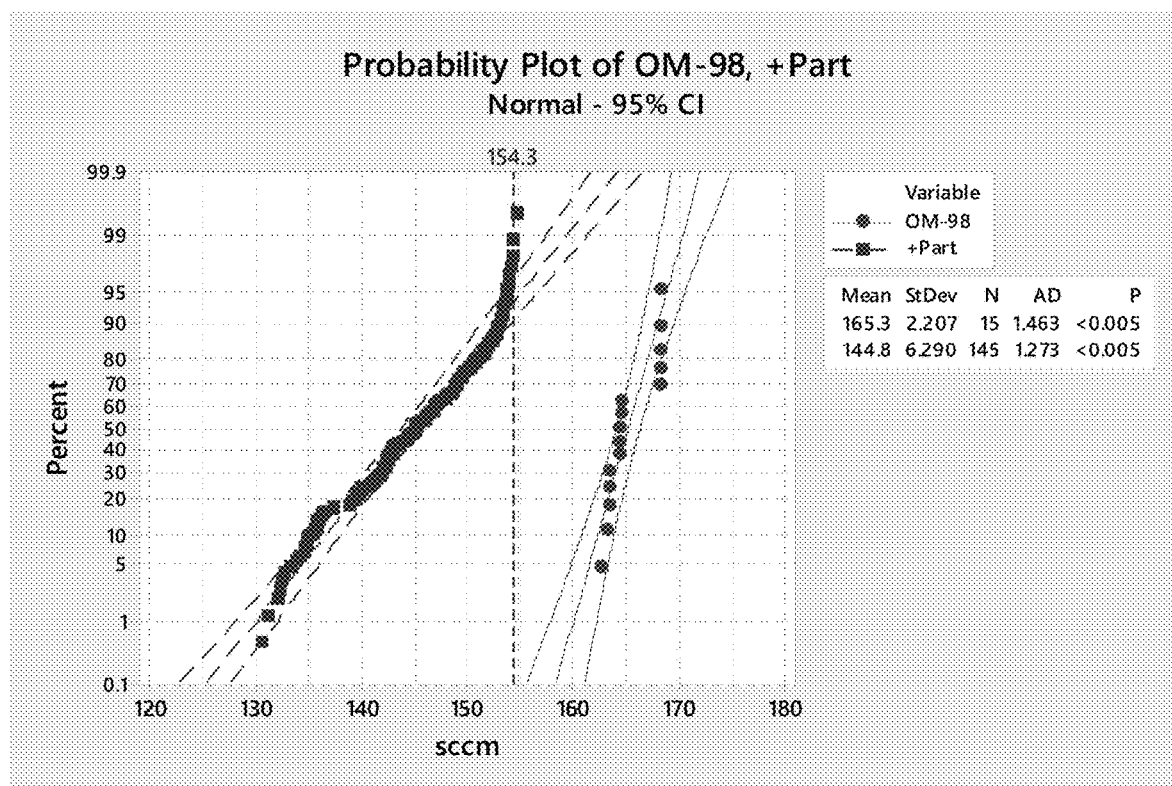
FIG. 16 shows mass flow rates for 98 cm original manufacturer (OM) devices without an occluding particulate and reprocessed devices inoculated with an occluding particulate (+Part). The occluded 95/90 UTL flow rate is shown, defining the acceptance criteria for 98 cm needles.
Figure 17:
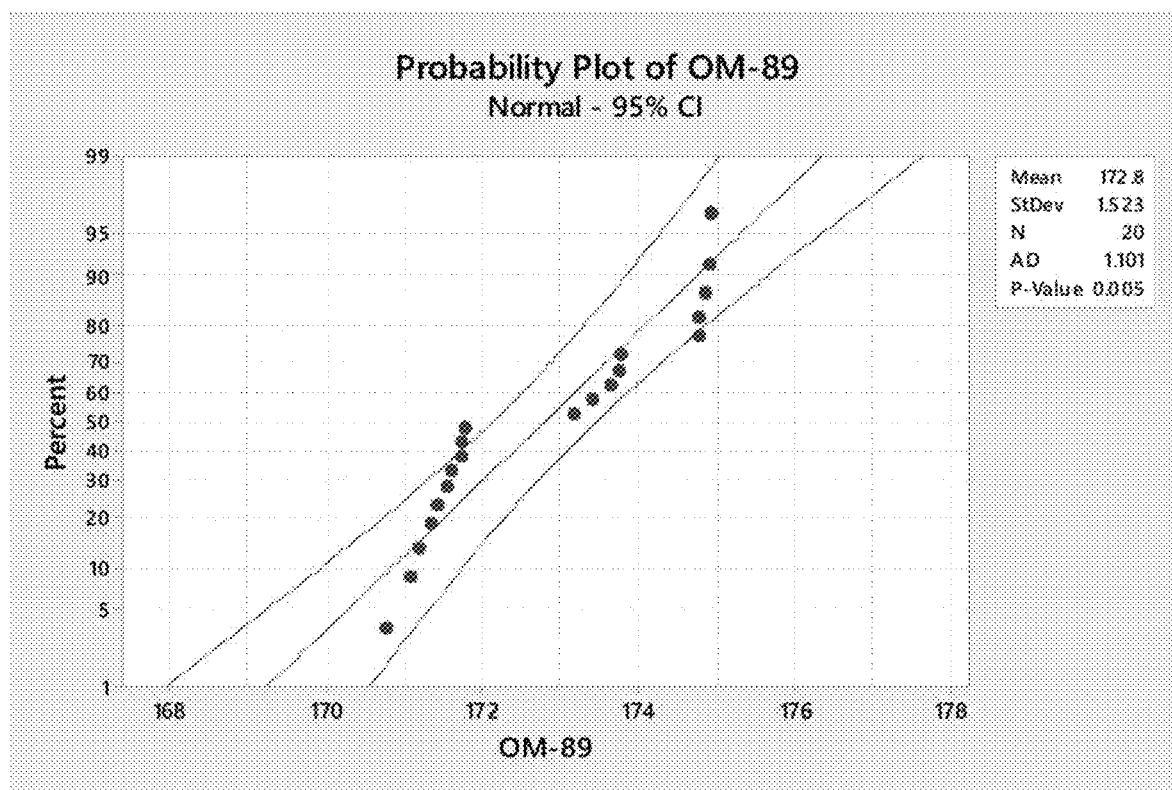
FIG. 17 is a distribution plot of OM mass flow characterization of the 89 cm needle.
Figure 18:
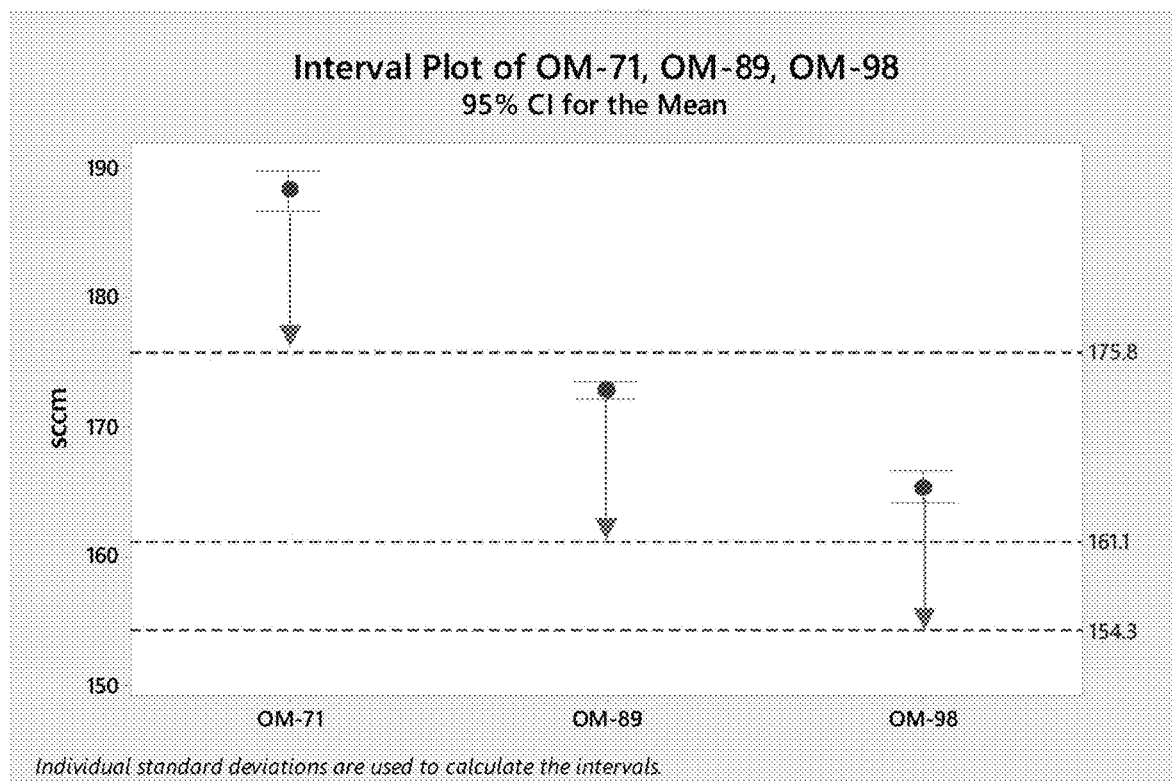
FIG. 18 are the mass flow rates for each OM size needle, with calculated acceptance criteria. For 89 cm needles, the acceptance criterion was derived from the average difference between OM 71 cm and OM 98 cm data and respective acceptance criteria.

The Mass Flow method described herein will be used to establish the test settings for in-process inspection of microlumen devices using the CTS Sentinel Blackbelt test system. The microlumen device used herein is a reprocessed Biosense Webster PentaRay EP catheter. Design characteristics of the device are shown in FIG. 8.

Methods

To define the parameters of the test method, occlusions were created by injecting 50 micron NIST traceable particle size standard polystyrene beads, suspended in bead solution containing ultrapure water, a dilute (<0.2%) aqueous polymeric adhesive and surfactant (<0.5%), into the lumen of each device and allowed to disperse throughout. The surfactant was included to prevent agglomeration in solution while the adhesive was used to lightly adhere the beads to the lumen wall following evaporation of the bead solution. Samples were oven incubated, removing residual moisture that could confound the data.

Control devices included unchallenged original manufacturer devices (OM), unchallenged reprocessed devices (REP), and reprocessed devices with bead solution (SHAM) containing no particles.

Solutions were prepared containing either $10^4$, $10^3$, 500, 100, 50, 5, 2, or 1 (per 100 µl solution) 50 micron bead(s). These were injected into the lumen of three devices per quantity (24 total samples with beads).

All samples were tested 5 times and the flow data recorded in standard cubic centimeters per minute (sccm).

Results

Data was recorded and analyzed in Excel (Microsoft Office 365) and Minitab 18. All statistical analysis was completed in Minitab 18 using the Smallest Extreme Distribution where applicable.

Control samples were tested, as shown in FIG. 1. There was no statistical difference between REP and SHAM devices. The OM devices performed over a lower and wider range, suggesting an artifact of the manufacturing process that is removed during reprocessing (or stretching of the lumen to a uniform diameter following clinical use of pressurized heparinized saline and subsequent reprocessing).

Figure 2:
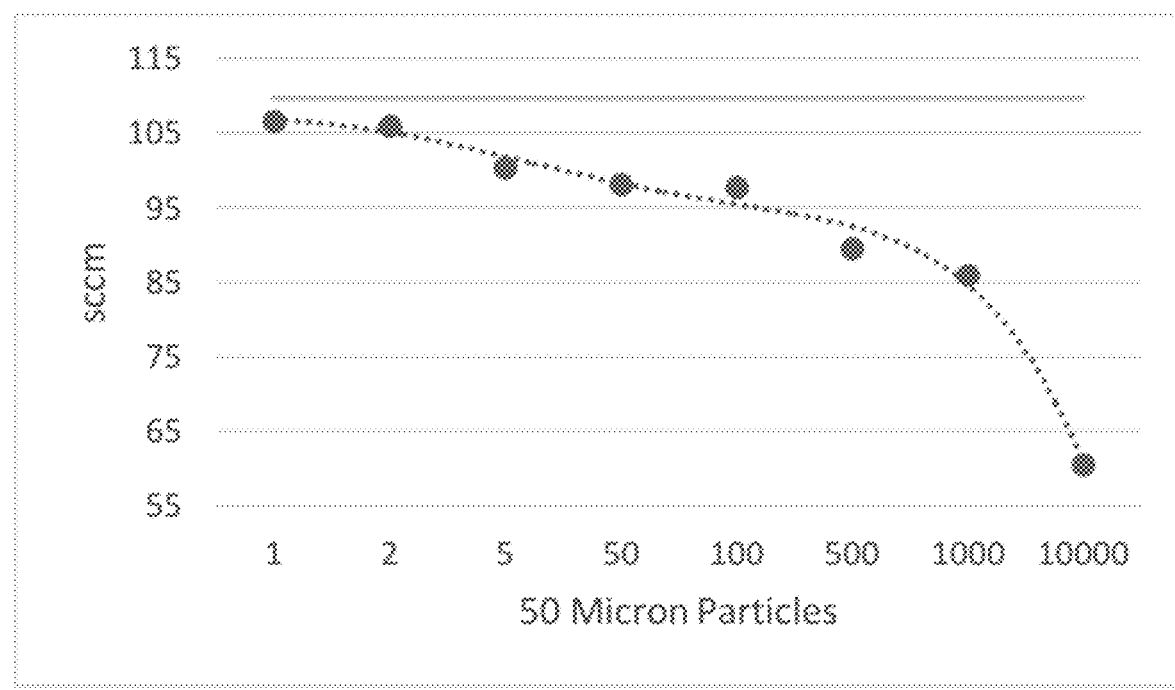
FIG. 2 is a graph showing the flow rate in sccm in devices loaded with an increasing number of 50 micron particles.

The average mass flow decreased (blue) as the quantity of particles increased, as expected, confirming that additional particles further occlude the lumen (FIG. 2). The yellow line reports the average data from the control samples, which proved significantly higher than any of the challenged devices. The average control device had a mass flow reading of 112.01 sccm, whereas the single particle challenged device averaged 106.68 sccm. This data also confirms that the mass flow test on the CTS Sentinel Blackbelt, as designed, is capable of detecting a single 50 micron particle.

Figure 3:
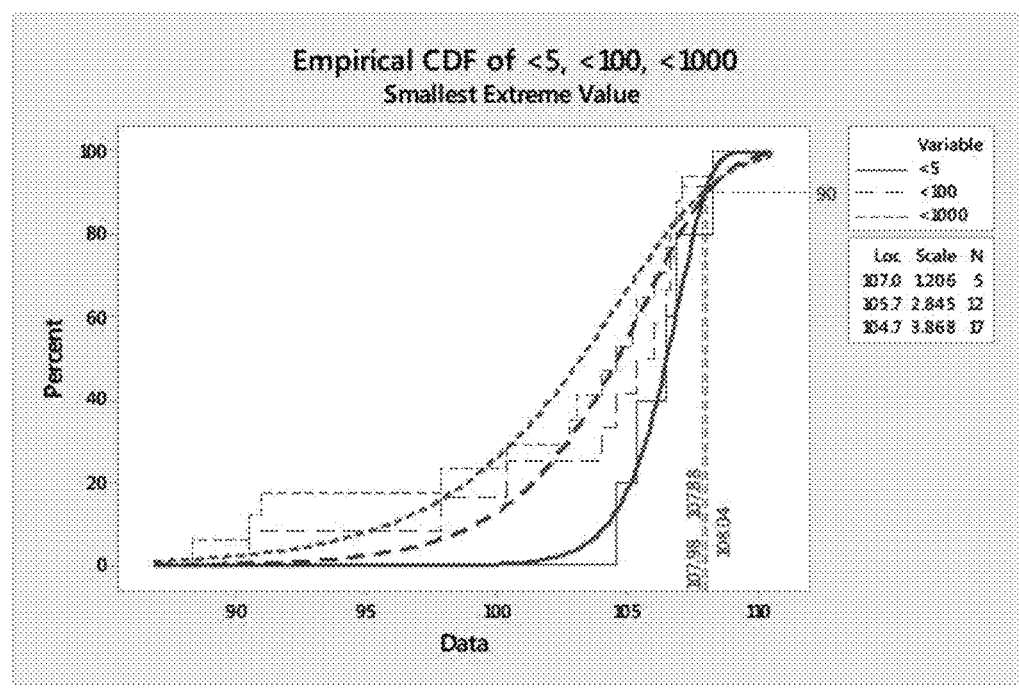
FIG. 3 depicts a cumulative distribution function (CDF) graph of grouped mass flow readings. Samples were grouped by devices containing less than 5, less than 100, and less than 1000 particles. Values displayed are the test limit parameter at 95/90 for each particular group, approximating 108 sccm.

A cumulative distribution function (CDF) was calculated from grouped flow rate data. Devices were grouped by those containing less than 1000 (N=17 devices), less than 100 (N=12 devices), and less than 5 particles (N=5 devices), and the 95/90 confidence interval test limits are shown, nearing 108 sccm (FIG. 3). The test limit parameter at 95/90 for each particular group, approximated 108 sccm. A probability plot focused on the group of devices containing 5 or fewer particles and compared them to the control devices (FIG. 4). The 95/90 values are shown, with the red line at 109.22 sccm incorporating in system error of 0.5% of full range, establishing the suggested test acceptance criteria. It is noted that this value is above the upper bound at 95/90, providing even more confidence to this defined parameter.

Figure 5:
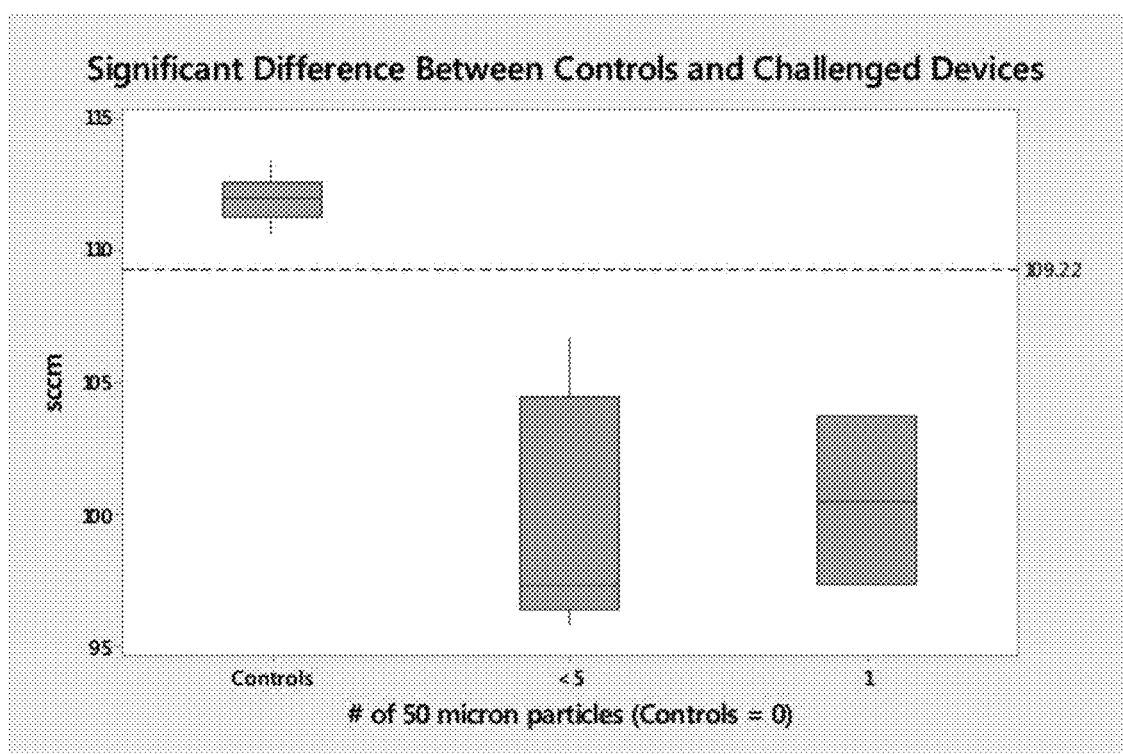
FIG. 5 is a plot showing the sccm of devices containing 5 or fewer, or a single 50 micron particle, and control devices. Dashed horizontal line represents the test acceptance criteria of 109.22 for the device.
Figure 6:
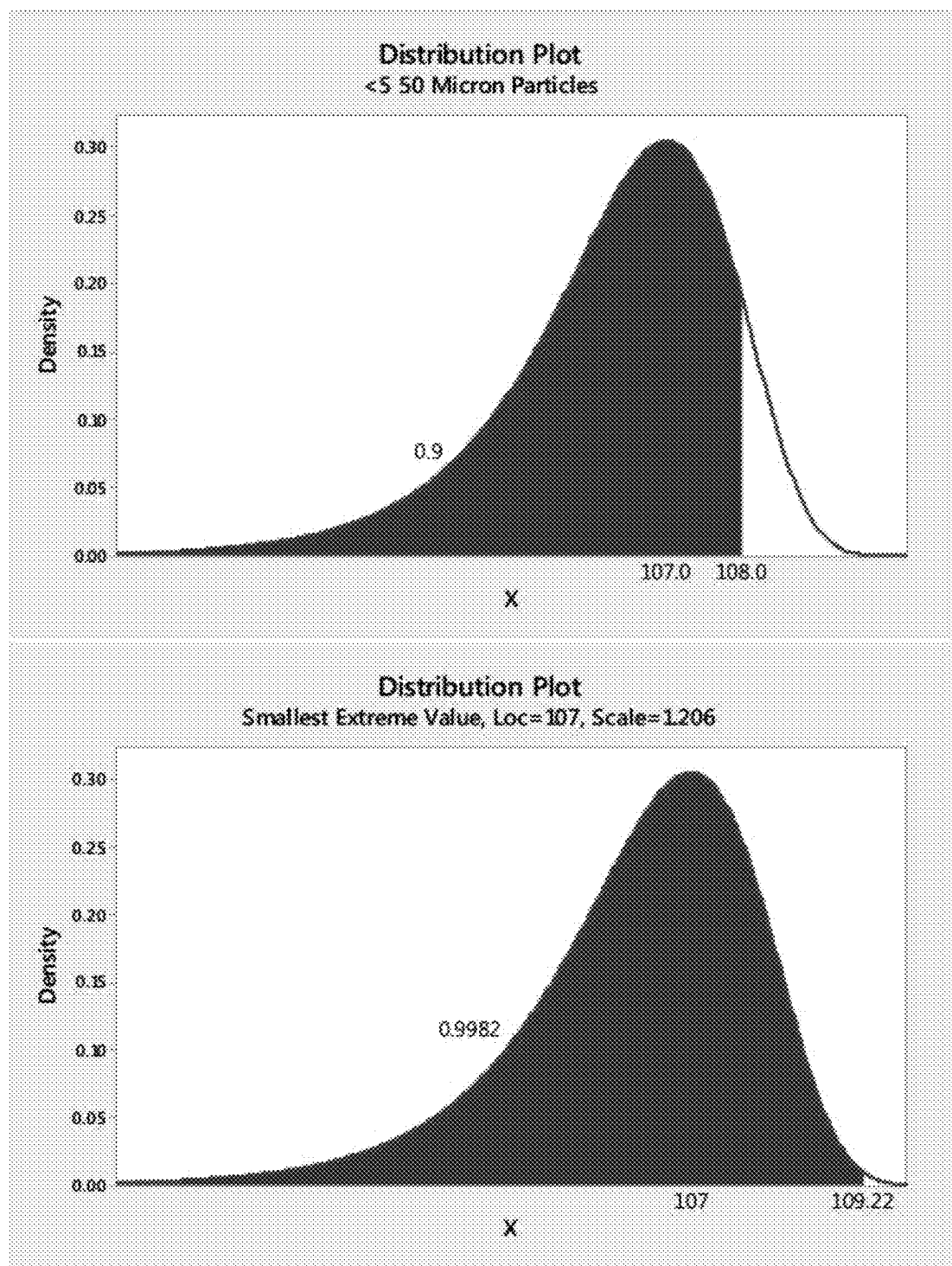
FIG. 6 are probability distribution plots of samples containing less than than 5 particles prior to (Top), and after (Bottom) adding in system error. With system error, the test acceptance criteria approximates 95/99.8.

As seen in FIG. 5, both the <5 and 1 particle devices provided mass flow readings that were considerably lower than the 109.22 sccm defined acceptance criteria. In process, this would result in these devices failing the lumen inspection test, and being rejected from further use. Applying a Probability Distribution Plot to the <5 micron particle data, the test acceptance criteria of 109.22 (95/90+system error) approximates 95/99.82, providing an even greater safety factor and confidence (FIG. 6).

Defined test parameters for the Biosense Webster PentaRay EP catheter are shown in Table 1.

| | |
|---|---|
| Prefill | 50% |
| Fill | 3.00 s |
| Test | 3.00 s |
| Exhaust | 0.50 s |
| Relax | 5.00 s |
| Minimum Change in Mass Flow (PASS) All data above this limit will pass | 109.23 sccm |
| Maximum Change in Mass Flow (FAIL) All data below this limit will fail | 109.22 sccm |

Conclusion

It is well understood that fewer large (>>200 micron) particles are required to create a similar embolic injury as smaller particles (<100 micron). However, the exact size, shape, or quantity of particles necessary remain unknown. While the clinical relevance of a single small embolic particle has not been established here, or elsewhere, it is generally accepted that, in accordance with minimizing periprocedural patient risk, reducing the amount and size of particles on or in a catheter or other EP instrument is a common goal shared by all device manufacturers. Out of an abundance of caution, to provide a considerable safety factor for all of our manufactured devices, we have selected 50 microns as the clinically relevant particle size to be used to define acceptance criteria.

This study was designed solely to develop a test method capable of identifying catheters with lumens containing unacceptable amounts of potentially embolic particles. During this process, it was important to investigate the scale and sensitivity of the test instrument, and then set the test acceptance criteria to an appropriately safe and statistically justifiable value. Production devices will encounter the same conservative test as part of an in-process inspection step, rejecting any that are tested to or below the acceptance criteria of 109.22.

Results from a previous study showed that this system is also capable of identifying devices occluded by single larger (200 micron) particle, with flow readings near 104 sccm. Additional confidence in this test method is provided by the fact that those flow values are only slightly lower than that achieved by devices occluded by 50 micron particles. Devices containing single (or multiple) larger particles would also be rejected by our acceptance criteria developed from the 50 micron particle data.

Full validation of the test conditions and acceptance criteria will be completed using a statistically significant sample set. A Nested Gage R&R will be performed by multiple independent operators using devices occluded in a consistent manner, validating the test program defined herein. This validation will be executed and reported prior to the submission for 510(k) approval of the PentaRay catheter, and a similar test method and subsequent validation developed and implemented during the investigation of other catheters containing microlumens.

Example 2. Occlusion Testing Criteria for Reprocessed Abbott (St. Jude Medical) Advisor HD Grid Mapping Catheters Occlusion testing acceptance criteria were defined for reprocessed Abbott (St. Jude Medical) Advisor HD Grid mapping catheters using the CTS Sentinel Blackbelt (CTS) tester. Specifications of the device are shown in Table 2.

TABLE 2

| Item Number | Description | Usable Length (cm) | French Size | Curve | Spacing (mm) | Electrodes | System Compatibility |
|---|---|---|---|---|---|---|---|
| D-AVHD-DF16 | Reprocessed Advisor HD Grid Mapping Catheter, Sensor Enabled | 110 | 8 F | DF | 3 | 16 | EnSite Velocity and EnSite Precision Cardiac Mapping Systems |

The CTS Sentinel Blackbelt Mass Flow Tester conducts leak and occlusion testing of small lumens. During mass flow testing, a device is initially charged to a set pressure and then the flow required to maintain that pressure is reported. Differences in this flow between the same type of device reflect restrictions in the lumen caused by occlusions, or other defects, that may negatively impact use of the device and may present potential patient risk. Flow-through devices of a different design or manufacturer may vary. However, provided the unimpeded flow of any subject device is within the performance range of the test system, the system can be adapted for inline inspection of production devices.

Per FDA recommendation, acceptance criteria required the identification of a single 50 um particle residing within the lumen of a reprocessed device and subsequent rejection of any device tested to retain such occlusions. Equipment capability, sensitivity, and test parameters were established in Example 1. The results of particulate identification testing, including the full test method validation, were recorded in Example 4.

Figure 7:
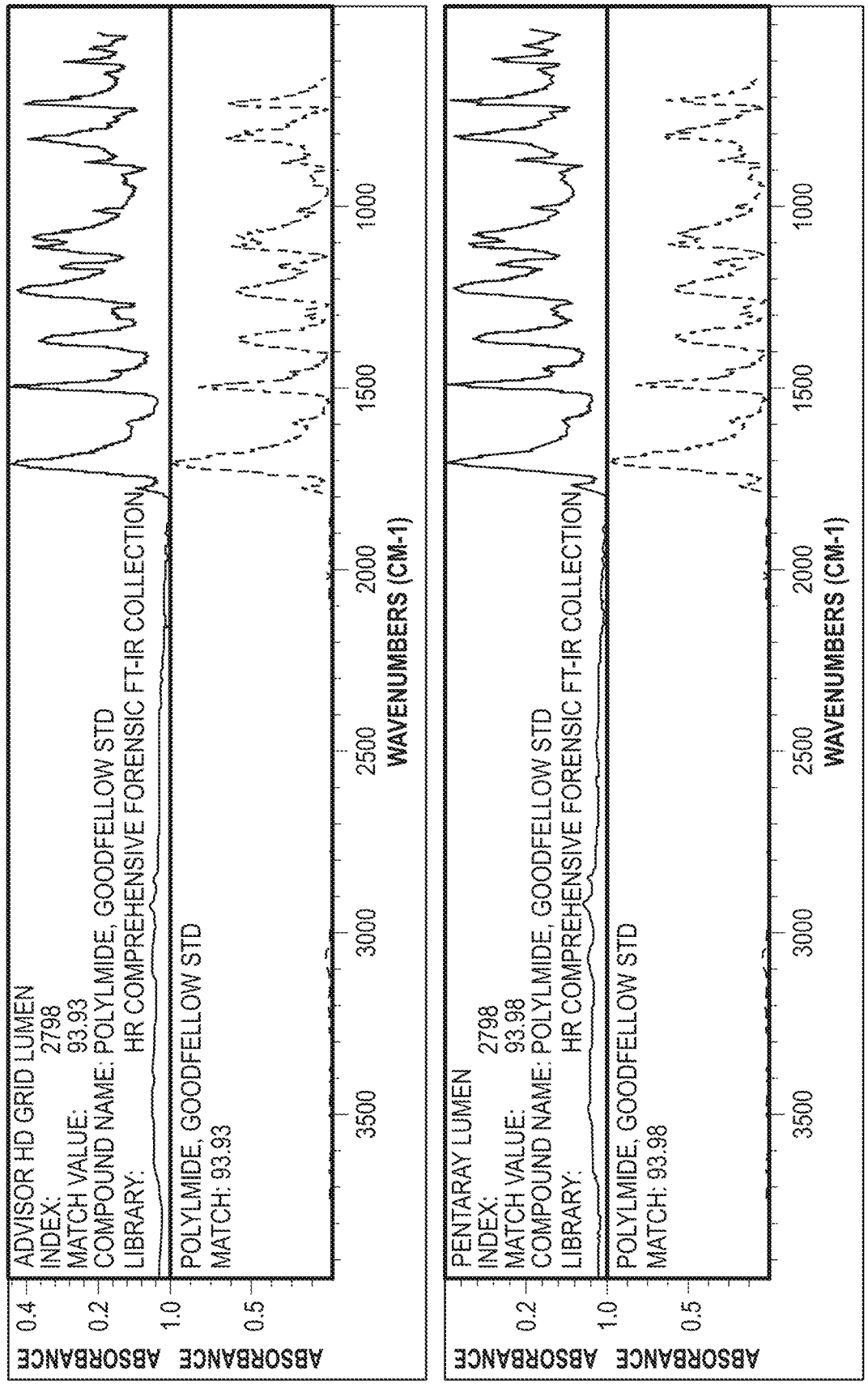
FIG. 7. FTIR Analysis of microlumens within the Advisor HD Grid and PentaRay catheters.

The Advisor HD Grid and PentaRay share similar design characteristics. Both devices contain a polyimide microlumen (FIG. 7) that runs from proximal sideport tubing at the handle through the shaft exiting at the distal tip (FIG. 8). The Advisor HD Grid has a slightly larger lumen diameter (0.018" I.D.) than the PentaRay (0.012" I.D.), and the PentRay has a slightly longer usable length (115 cm) versus the Advisor HD Grid (110 cm). The Advisor HD Grid also has a perforated cap over the lumen at the distal tip, whereas the PentaRay terminates in an open lumen. All of these properties affect the flow rate necessary to maintain the set pressure, which is why characterization of a subject device is required in the development of device-specific test acceptance criteria.

Understanding that flow characteristics are unique to each device, the data from the study conducted herein will be used to define acceptance criteria for the Advisor HD Grid. Flow Characterization and Occlusion.

Samples selected included sixty-eight (68) clinically-used and reprocessed devices and two (2) original manufacturer (OM) devices. On the CTS system, using a new program with no acceptance criteria, initial characterization of the two OM and fifty-eight of the reprocessed devices was performed to assess the non-occluded flow rate. Fifty-eight reprocessed devices were then prepared, inoculating a single 50 μm bead into the lumen at the proximal end and then incubated a minimum of 48 hours at 65° C. prior to testing (to ensure the evaporation of the bead buffer solution which might otherwise affect test results).

Ten (10) reprocessed devices were inoculated with the bead buffer solution alone (no particulate) to serve as carrier controls. Following incubation, the devices were analyzed on the CTS, recording a single flow measurement for each sample.

Results are shown in FIGS. 9A-C to FIG. 13. Data was analyzed in Minitab 18. At 95/95 confidence, the upper bound of the probability plot for the devices containing a particulate defines the acceptance criteria.

Therefore, acceptance criteria for the Advisor HD Grid device is 157.32 sccm. Advisor HD Grid devices that test at or below these measurements will FAIL. Devices that test above these measurements will PASS.

Example 3. Occlusion Testing Acceptance Criteria for Reprocessed St. Jude Medical BRK Transseptal Needles Using the CTS Sentinel Blackbelt (CTS) Tester Specifications of the device are shown in Table 3.

TABLE 3

| OEM Product Device | OEM Product Code | Needle Gauge Size | Bevel Angle | Curve Type | Usable Length (cm) |
|---|---|---|---|---|---|
| St. Jude Transseptal Medical BRK Needle | 407200 407201 | 18 ga | 50° | BRK BRK-1 | 71 71 |

TABLE 3-continued

| OEM Product Device | OEM Product Code | Needle Gauge Size | Bevel Angle | Curve Type | Usable Length (cm) |
|---|---|---|---|---|---|
| Transseptal Needles | 407205 | | | BRK | 89 |
| | G407215 | | | BRK-1 | 89 |
| | 407206 | | | BRK | 98 |
| | 407207 | | | BRK-1 | 98 |
| St. Jude Medical BRK XS Transseptal Needles | G407208 | | 30° | BRK XS | 71 |
| | G407209 | | | BRK-1 XS | 71 |
| | G407210 | | | BRK XS | 89 |
| | G407216 | | | BRK-1 XS | 89 |
| | G407211 | | | BRK XS | 98 |
| | G407212 | | | BRK-1 XS | 98 |

Devices were reprocessed and inoculated with a single 50 μm bead into the lumen of OM and clinically-used, reprocessed devices. Devices were incubated a minimum of 48 hours at 65° C. prior to testing. On the CTS system, using a new program with no acceptance criteria, initial characterization of an OM, non-occluded device was conducted to establish the flow rate range for both 71 and 98 cm devices. Challenged devices were then analyzed and 5 measurements recorded for each sample. Each sample was tested five (5) times. The number of unique samples tested can be calculated by dividing the data points (N) shown by five (5). Data was analyzed in Minitab 18. A 95/90 Confidence Interval is used to define the acceptance criteria for each needle. Results are shown in FIGS. 14A-C to FIG. 18.

Test program acceptance criteria is unique to the length of the needle, and is defined as shown in Table 4.

TABLE 4

| Needle size (cm) | Flow rate acceptance criteria (sccm) |
|---|---|
| 71 | 175.8 |
| 89 | 161.1 |
| 98 | 154.3 |

Respective devices that test at or below these measurements will FAIL. Devices that test above these measurements will PASS.

Example 4. Detecting a Single 50 Um Particle in Small Lumens

The purpose of this report is to provide documented evidence that the OTS Sentinel Blackbelt (TS) tester using the small lumen occlusion test method and parameters defined in Example 1 is capable of reliably detecting a single 50 um occlusion in small lumens (similar to those found in the PentaRay family of products).

The study used the following subject device:

TABLE 5

| Device Scope | |
|---|---|
| Original Manufacturer (OM): | Biosense Webster |
| OM Description: | PentaRay Nav eco High-Density Mapping Catheter |
| OM Item Number(s): | See Table 2 below. |
| Device Used: | D128207, D128208, D128210, D128211 |

TABLE 6

| Item Numbers | | | | | | |
|---|---|---|---|---|---|---|
| Item Number | Description | Usable Length (cm) | French Size | Curve | Spacing (mm) | Electrodes |
| D128207 | PentaRay Nav eco High-Density | 115 | 7 F | F | 4-4-4 | 20 |
| D128208 | PentaRay Nav eco High-Density | 115 | 7 F | F | 2-6-2 | 20 |
| D128210 | PentaRay Nav eco High-Density | 115 | 7 F | D | 4-4-4 | 20 |
| D128211 | PentaRay Nav eco High-Density | 115 | 7 F | D | 2-6-2 | 20 |

Equipment List (as Below or Equivalent/Similar)

| | |
|---|---|
| 6.1 | 1 ml 28G × ½" disposable syringe (10049962) |
| 6.2 | 50 ml Conical (43237-2) |
| 6.3 | Bangs Bead Solution with 0.1% surfactant (SOLN1) |
| 6.4 | Polyvinylpyrrolidone (PVP40-50G) |
| 6.5 | 50 um Particle Size-Standard Solution (64190-15) |
| 6.6 | 4-2500X Compound Microscope (B120C-E1) |
| 6.7 | 1.3 MP Digital Camera (MD130) |
| 6.8 | 0-6X Celestron Microscope (44308) |
| 6.9 | Particle Trap Plates |
| 6.10 | Single Channel Pipettors & Disposable Tips |
| 6.11 | CTS Sentinel Blackbelt with Mass Flow Sensor |
| 6.12 | PentaRay Occlusion Test Fixture (T-0056) |

Sample Device Collection and Processing:

Devices that were used for this study include sixty-eight (68) clinically used (natively soiled) reprocessed PentaRay devices received from various collection sites covering all item numbers listing in the scope (Table 5). Twenty-Nine (29) devices were inoculated with a single 50 um particle as described in Example 1. Twenty-Nine (29) devices were left unchallenged following reprocessing. The remaining ten (10) devices were challenged with bead buffer alone (SHAM).

Figure 19:
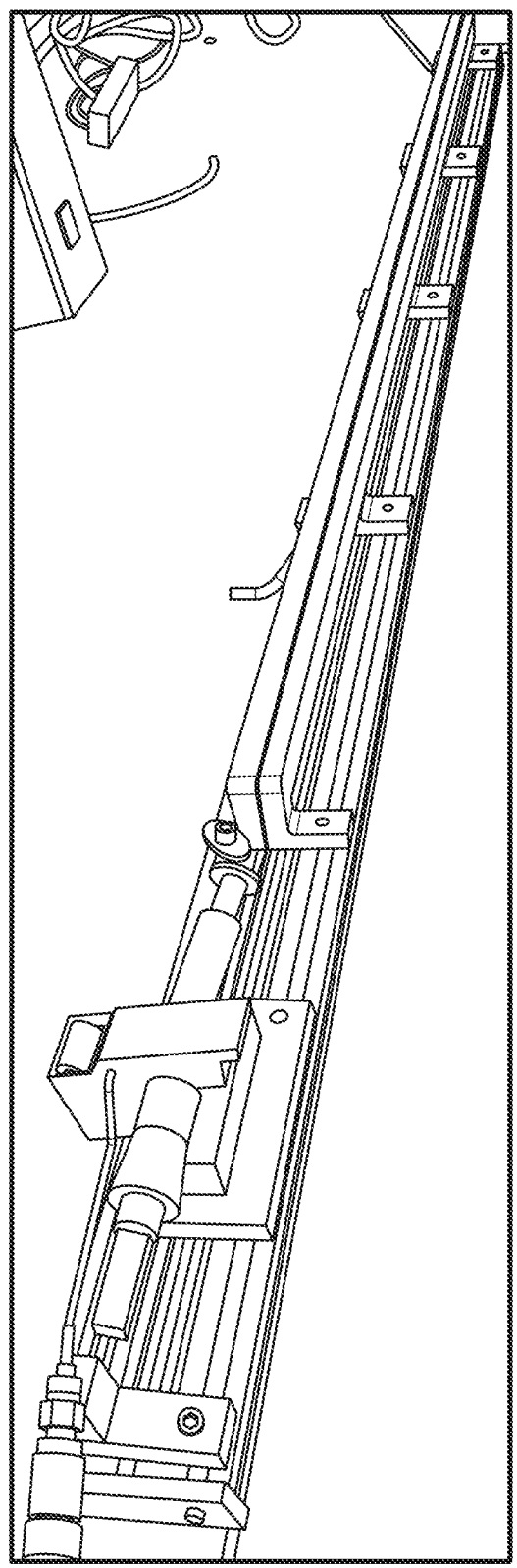
FIG. 19. Image of test fixture.
Figure 20:
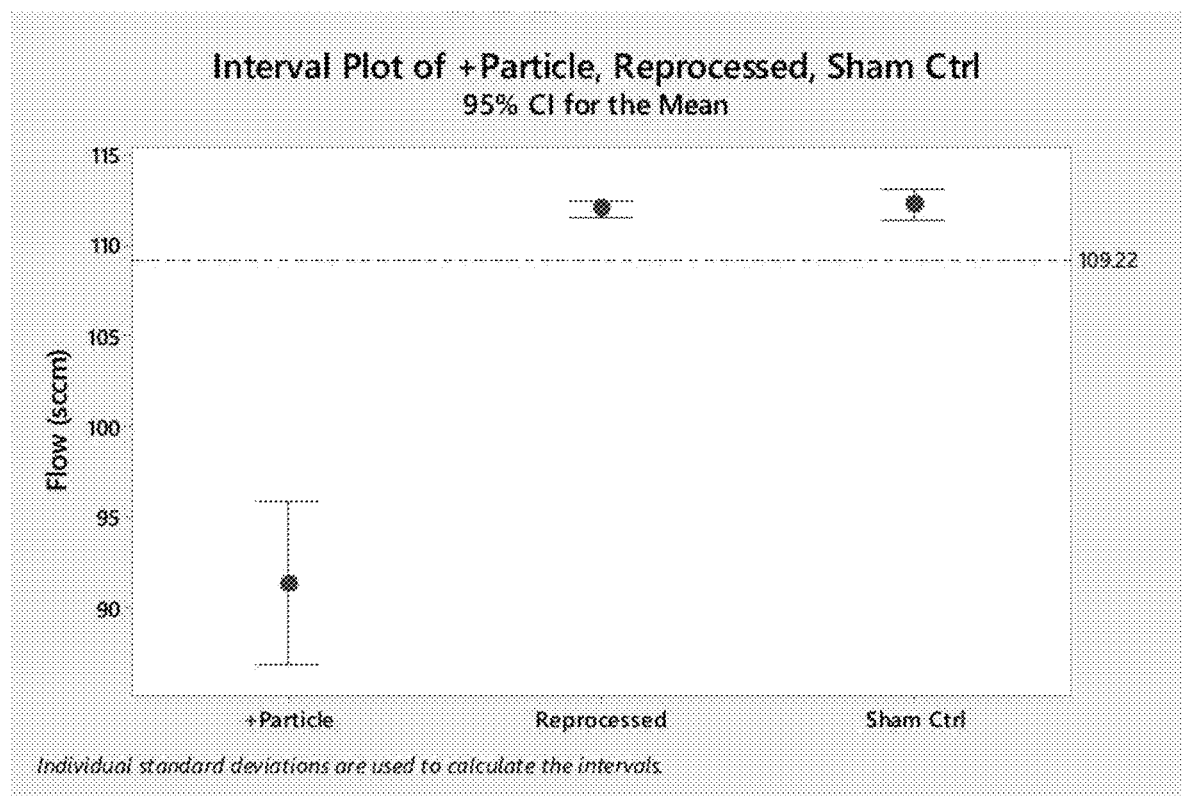
FIG. 20. Mass Flow readings for devices challenged with a single 50 um particle, reprocessed (unchallenged devices), and Sham Control devices (challenged with bead buffer alone). 109.22 sccm was defined as the test acceptance criteria during test method development (Example 1).

A test fixture (T-0056; FIG. 19) was utilized to straighten each device shaft during testing, reducing variability introduced by random positioning. The distal tip of the device was shielded with an open-bottom conical tube positioned against the particle trap plate, which allowed the recovery of a particle exhausted from the lumen during testing.

Inoculation, syringe, and lumen flushing images were recorded using 4-2500× magnification on an AmScope microscope fitted with a 1.3 MP digital zoom capable camera. Particle traps were analyzed and images recorded using 0-60× magnification provided by a Celestron microscope.

Acceptance Criteria:

TEST PROGRAM acceptance criteria is defined to be 109.22 (Standard Cubic Centimeters per Minute) sccm, as documented in Example 1.

Mass Flow>109.22 sccm=PASS

Mass Flow≤109.22 sccm=FAIL

Known Good devices PASS, known bad devices (challenged with a single 50 μm particle) FAIL, and the study shall achieve 95/90 confidence.

Deviation:
Data was analyzed in Minitab18 to 95% confidence.
Results:
Results are shown in FIG. 20 to FIG. 24.

Discussion

Figure 21:
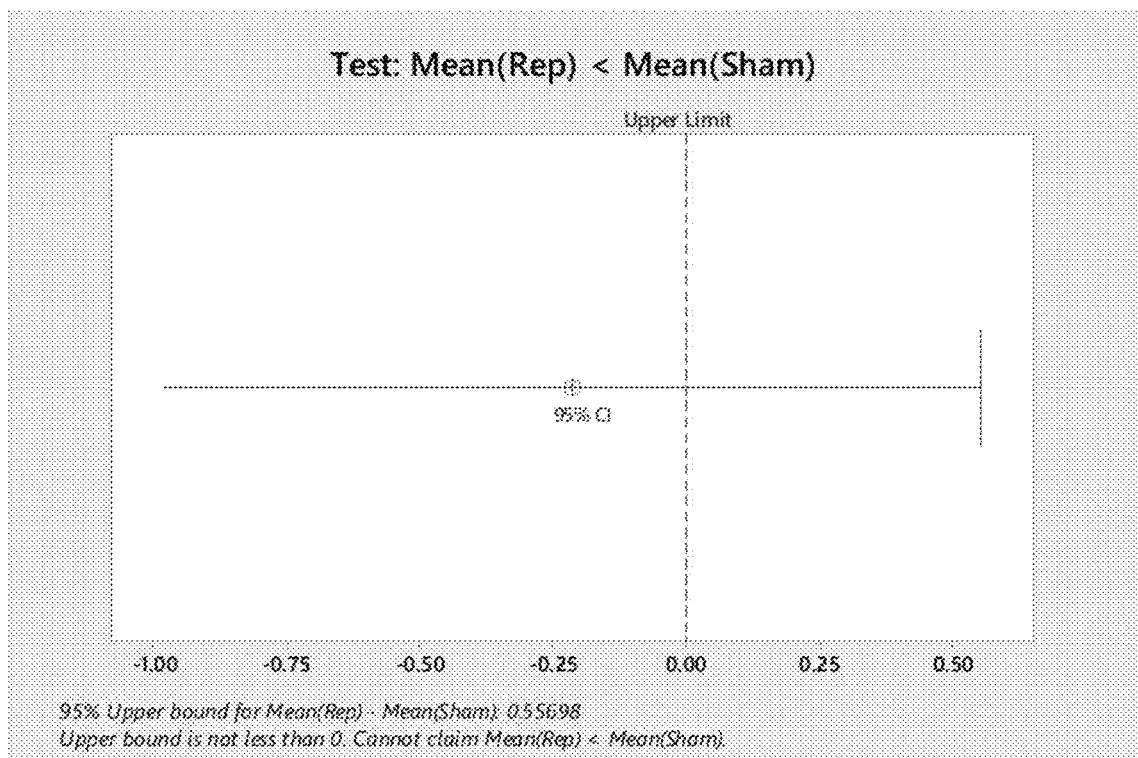
FIG. 21. No statistical difference in mass flow readings noted between unchallenged reprocessed device and sham control (challenged with bead buffer only) devices.
Figure 22:
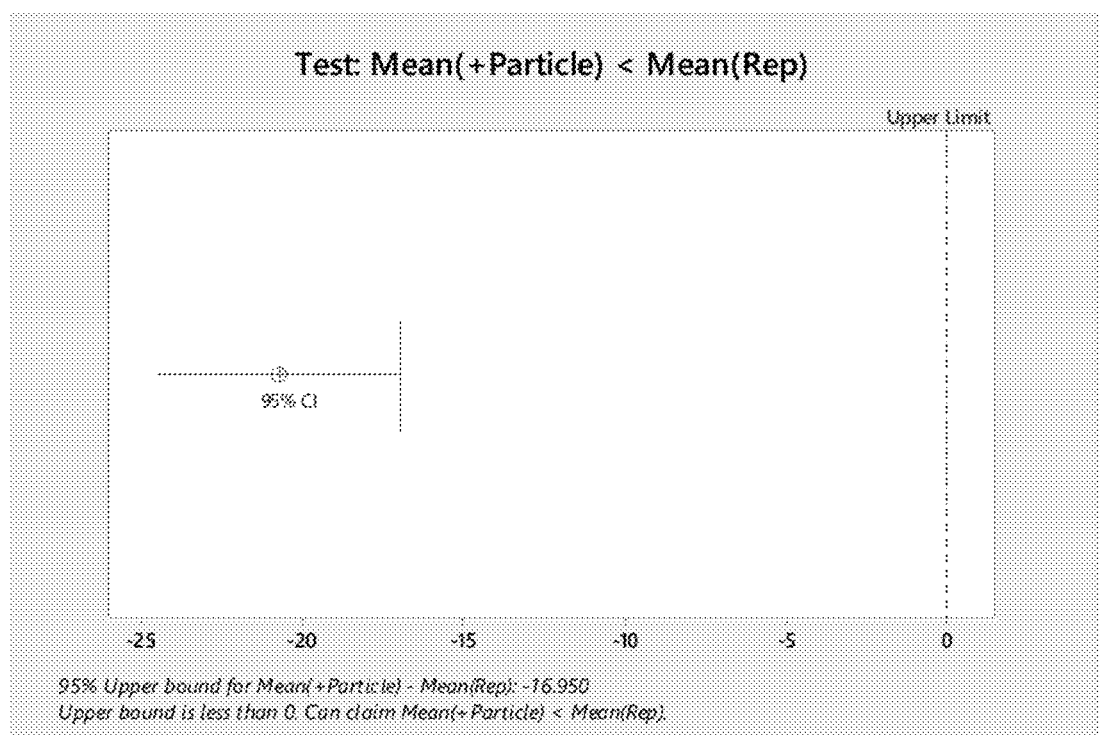
FIG. 22. A statistical difference noted in mass flow readings between unchallenged reprocessed devices and those challenged with a single 50 um particle.

As observed in the interval plot (FIG. 20), all mass flow data for the unchallenged reprocessed samples and sham control sets are above the test acceptance limit, while the challenged device data points are well below the acceptance limit. There was no statistically significant difference between mass flow readings among the unchallenged reprocessed and sham (challenged with bead buffer alone) sample sets (FIG. 21). However, there was a remarkable difference between unchallenged reprocessed and challenged sample sets (FIG. 22).

Figure 23:
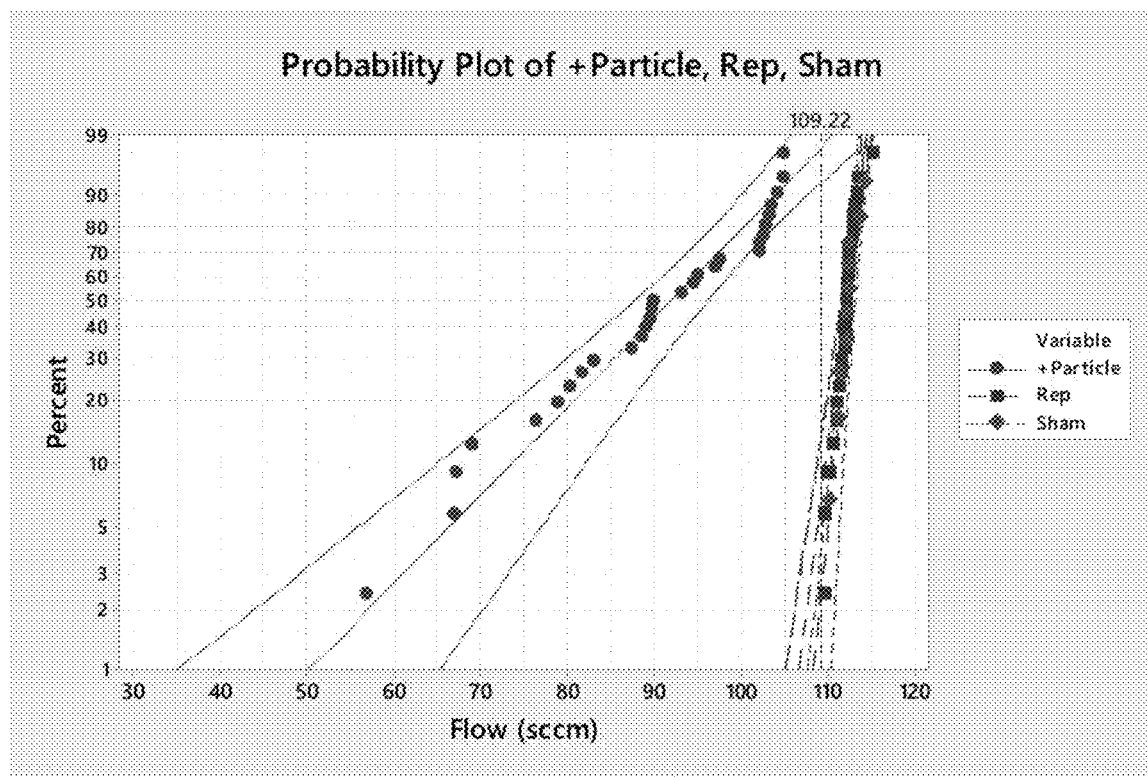
FIG. 23. A probability plot suggests that the acceptance criterion (109.22 sccm) is more conservative than that reported at the 95%/90% Upper Bound (107.66 sccm) for challenged devices. All control and unchallenged samples record mass flow readings higher than the acceptance criterion, while all challenged devices record readings well below the acceptance criterion.
Figure 24:
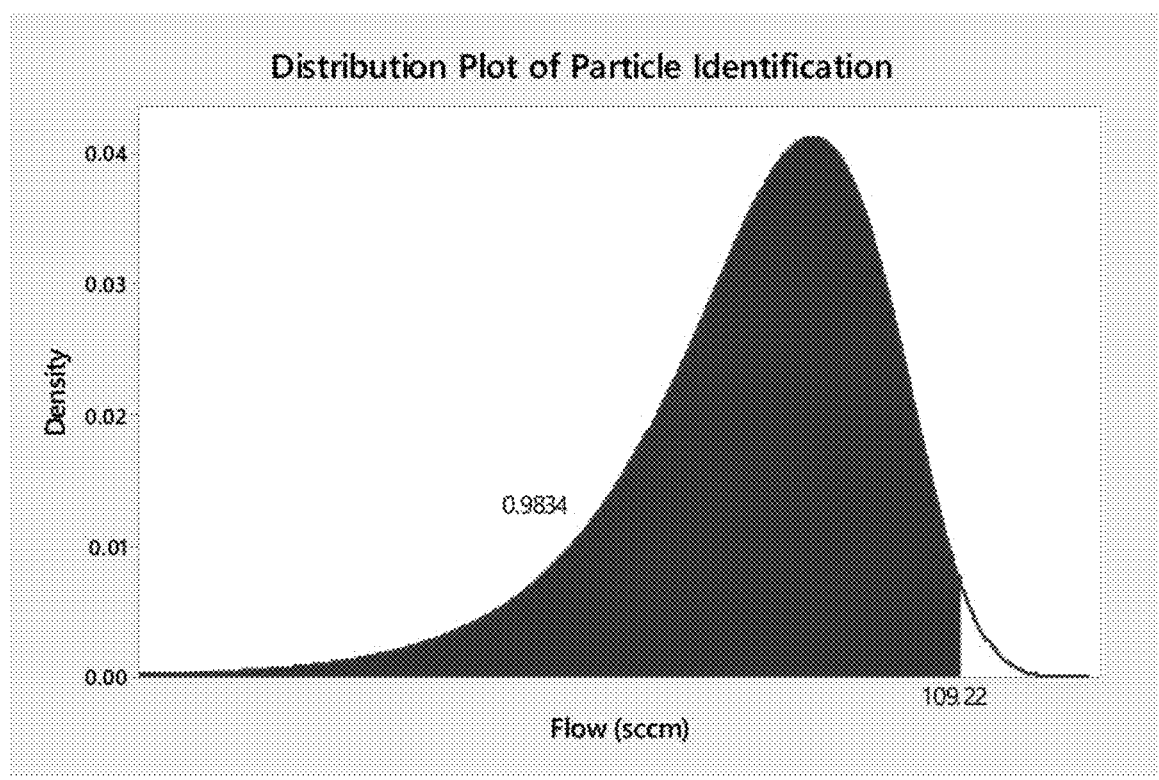
FIG. 24. A probability plot suggests that production devices containing a single 50 um occluding particle will test at a 95%/98.3% confidence interval when applying the following acceptance criterion of Mass Flow ≤ 109.22 sccm=FAIL.

The 95%/90% upper bound of the probability plot for the challenged device data recommends a test acceptance limit of 107.66 sccm (FIG. 23). Retaining the 109.22 sccm test limit defined during test method development exceeds 95%/98% (FIG. 24). This further suggests that the defined test acceptance limit is quite conservative and includes a considerable safety factor.

Figure 25:
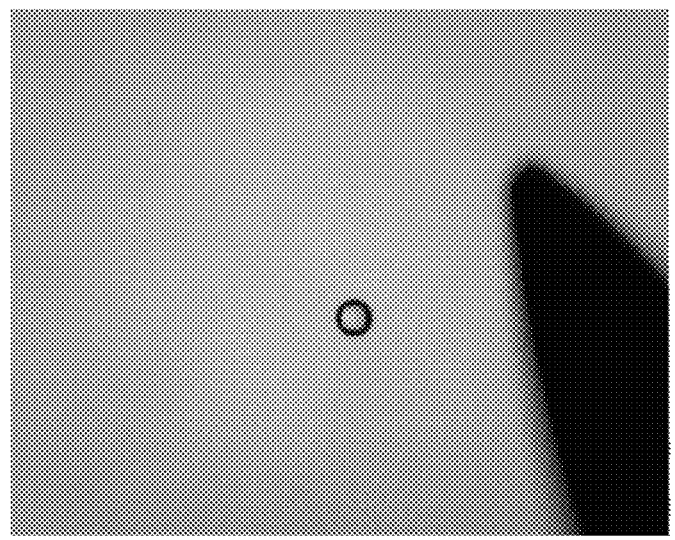
FIG. 25. Images of an isolated particle prior to testing (top) and flush fluid after testing (bottom).
Figure 25:
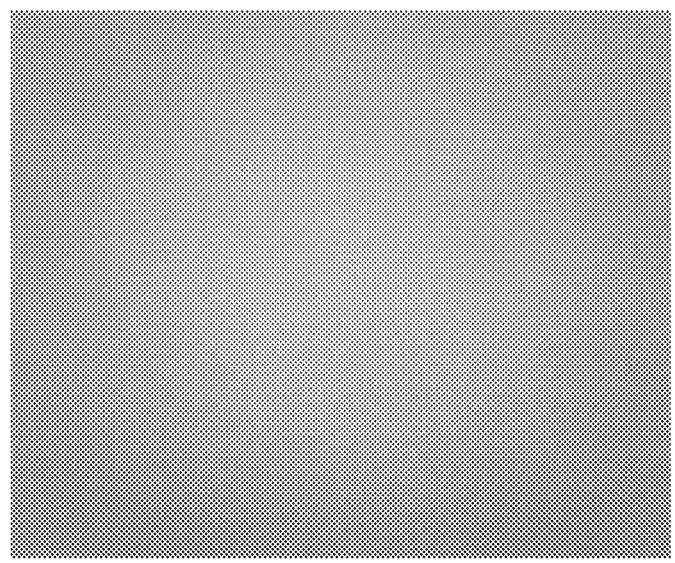

Magnified images taken both prior to and following inoculation and testing (Example in FIG. 25) provide evidence that test conditions involved a single particle inoculated within the lumen of challenged devices. It is of interest that devices that exhausted the particle during testing (where the particle was observed in the particle trap following testing) experienced a measurably higher flow rate than those that retained the particle (as evidenced by the absence of a particle on the particle trap, but its presence in the lumen flush fluid). The objective of this study was to develop an inline inspection test capable of detecting and rejecting devices that contain a single 50 um particle within the lumen of a reprocessed device.

Conclusion

This study was conducted at a 95%/90% confidence interval to validate the acceptance criterion for the small lumen occlusion test. This confidence interval required 29 of 29 challenged samples to FAIL (read at or lower than 109.22 sccm) and 29 of 29 unchallenged reprocessed samples to PASS (read higher than 109.22 sccm). This was achieved, signifying that the CTS mass flow tester is capable of reliably detecting occlusions as small as a single 50 um particle in lumens of reprocessed subject devices. It also confirms that this test program is capable of reliably rejecting devices that contain such occlusions.

REFERENCES

1. Horowitz, L. N.; Kay, H. R.; Kutalek, S. P.; Discigil, K. F.; Webb, C. R.; Greenspan, A. M.; Spielman, S. R. Journal of the American College of Cardiology 1987, 9 (6), 1261-1268.
2. Haghjoo, M.; Vasheghani-Farahani, A.; Shafiee, A.; Akbarzadeh, M.; Bahrololoumi-Bafruee, N.; Alizadeh-Diz, A.; Emkanjoo, Z.; Fazelifar, A.; Bakhshandeh, H. Research in Cardiovascular Medicine 2018, 7 (1), 20.
3. Electrophysiological Studies. Hopkins medicine test_procedures cardiovascular electrophysiologic al_studies_92, p 07971 (accessed Dec. 18, 2018).
4. USP<788> PARTICULATE MATTER IN INJECTIONS, The United States Pharmacopeial Convention, 2018
5. Langille, S. PDA Journal of Pharmaceutical Science and Technology 2013, 67, 186-200.
6. Puntis, J.; Wilkins, K.; Ball, P.; Rushton, D.; Booth, I. Archives of Disease in Childhood 1992, 67, 1475-1477.
7. Mettler, F.; Guiberteau, M. Essentials of nuclear medicine imaging; Elsevier Saunders: Philadelphia, 2012.
8. AAMI TIR42:2010, Evaluation of Particulates Associated With Vascular Medical Devices
9. Food and Drug Administration (FDA). Coronary, Peripheral, and Neurovascular Guidewires-Performance Tests and Recommended Labeleing; 2018.
10. Haines, D.; Stewart, M.; Ahlberg, S.; Barka, N.; Condie, C.; Fiedler, G.; Kirchhof, N.; Halimi, F.; Deneke, T. Circulation: Arrhythmia and Electrophysiology 2013, 6, 16-22.
11. Haines, D.; Stewart, M.; Barka, N.; Kirchhof, N.; Lentz, L.; Reinking, N.; Urban, J.; Halimi, F.; Deneke, T.; Kanal, E. Circulation: Arrhythmia and Electrophysiology 2013, 6, 23-30.
12. Rapp, J.; Pan, X.; Sharp, F.; Shah, D.; Wille, G.; Velez, P.; Troyer, A.; Higashida, R.; Saloner, D. Journal of Vascular Surgery 2000, 32, 68-76.
13. Reina-De La Torre, F.; Rodriguez-Baeza, A.; Sahuquillo-Barris, J. The Anatomical Record 1998, 251, 87-96.

What is claimed is:

1. A method of determining acceptance criteria for identification of an occluding particle in a lumen of a device to be inspected, the method comprising:
   a. obtaining or having obtained a mass flow measurement for a representative device occluded with a defined number of one or more occluding particles; and
   b. calculating an upper test limit mass flow rate for the occluded representative device;
wherein the upper test limit mass flow rate is the acceptance criteria, and wherein an inspected device is determined to be occluded if a mass flow measurement for the inspected device is equal to or lower than the acceptance criteria, and the inspected device is determined to be unoccluded if the mass flow measurement in the inspected device is higher than the acceptance criteria.

2. The method of claim 1, wherein the device is a medical device, a biological analysis device, a cell culture device, a cell separation device, a nucleic acid sequencing device, or a device in the electronics industry.

3. The method of claim 1, wherein the upper test limit mass flow rate for the occluded representative device is an upper boundary of a probability plot calculated using a mass flow measurement of a representative device occluded with a defined number of one or more occluding particles.

4. The method of claim 1, further comprising occluding the lumen of the representative device with the defined number of particles.

5. The method of claim 4, further comprising isolating the defined number of one or more occluding test particles.

6. The method of claim 5, wherein a single particle is isolated.

7. The method of claim 5, wherein isolating a defined number of particles comprises:
   a. suspending particles in a bead solution comprising a surfactant and aqueous polymeric adhesive; and
   b. isolating one or more single particles under magnification into a bead solution.

8. The method of claim 7, wherein the bead solution is a buffered bead solution comprising an aqueous polymeric adhesive and a surfactant.

9. The method of claim 4, wherein the representative device is occluded by adhering the particles in the lumen of the representative device.

10. The method of claim 9, wherein adhering the particles in the lumen of the representative device comprises:
   a. injecting the particle into the lumen of the representative device; and
   b. drying the lumen.

11. The method of claim 10, wherein the lumen is dried by incubating the device in a recirculating air oven for about 48 hours at about 65° C.

12. The method of claim 1, wherein the mass flow measurement for the representative device is obtained using a method comprising:
   a. charging the lumen with air to a predetermined pressure; and
   b. measuring the flow of air sufficient to maintain the pressure over a preset period of time to obtain the mass flow measurement.

13. An inspection method for accepting a device comprising a lumen as unoccluded or rejecting the device as occluded, the method comprising:
   a. obtaining or having obtained a mass flow measurement of the device to be inspected;
   b. comparing the mass flow measurement in the device to an upper test limit mass flow rate calculated for an occluded representative device; and
   C. accepting the device as unoccluded if the mass flow measurement in the inspected device is higher than the upper test limit mass flow rate, and rejecting the device as occluded if the mass flow measurement in the inspected device is equal to or lower than the upper test limit mass flow rate.

14. The inspection method of claim 13, wherein the upper test limit mass flow rate for the occluded representative device is an upper boundary of a probability plot calculated using a mass flow measurement of a representative device occluded with a defined number of one or more occluding particles.

15. The inspection method of claim 14, wherein the upper boundary of the probability plot is calculated using a method comprising:
   a. occluding the lumen of a representative device with the defined number of particles by adhering the particles in the lumen of the representative device;
   b. obtaining a mass flow measurement for the occluded representative device; and
   C. calculating the upper boundary of a probability plot using the mass flow measurement obtained in step (b).

16. The inspection method of claim 15, wherein the upper boundary of the probability plot is calculated at a 95/85 confidence interval or higher.

17. The inspection method of claim 13, wherein the device is a clinically used reprocessed medical device.

18. The inspection method of claim 17, further comprising re-using the device in the clinic.

19. The method of claim 17, wherein the medical device is a device used during electrophysiological procedures.

* * * * *